United States Patent
Aoki

(10) Patent No.: US 10,792,476 B2
(45) Date of Patent: Oct. 6, 2020

(54) GUIDE WIRE

(71) Applicant: TERUMO KABUSHIKI KAISHA, Shibuya-ku, Tokyo (JP)

(72) Inventor: Teruo Aoki, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 301 days.

(21) Appl. No.: 15/788,893

(22) Filed: Oct. 20, 2017

(65) Prior Publication Data

US 2018/0140802 A1 May 24, 2018

(30) Foreign Application Priority Data

Nov. 18, 2016 (JP) ................. 2016-225474

(51) Int. Cl.
*A61M 25/09* (2006.01)

(52) U.S. Cl.
CPC ........ *A61M 25/0905* (2013.01); *A61M 25/09* (2013.01); *A61M 2025/09058* (2013.01); *A61M 2025/09083* (2013.01); *A61M 2025/09133* (2013.01); *A61M 2025/09166* (2013.01); *A61M 2025/09175* (2013.01)

(58) Field of Classification Search
CPC .......................... A61M 25/0905; A61M 25/09
USPC ....................................................... 600/585
See application file for complete search history.

(56) References Cited

U.S. PATENT DOCUMENTS

| 5,678,296 A * | 10/1997 | Fleischhacker .... A61B 17/3207 29/450 |
| 2006/0241419 A1 * | 10/2006 | Satou .................... A61M 25/09 600/434 |
| 2008/0161726 A1 | 7/2008 | Itou |
| 2011/0015618 A1 | 1/2011 | Satou et al. |
| 2012/0029476 A1 * | 2/2012 | Kanazawa ............ A61M 25/09 604/528 |

FOREIGN PATENT DOCUMENTS

| JP | 2008-178656 A | 8/2008 |
| WO | 2009/039063 A1 | 3/2009 |

OTHER PUBLICATIONS

The extended European Search Report dated Apr. 17, 2018, by the European Patent Office in corresponding European Patent Application No. 17198696.1-1132. (5 pages).

* cited by examiner

*Primary Examiner* — Daniel L Cerioni
(74) *Attorney, Agent, or Firm* — Buchanan Ingersoll & Rooney PC

(57) ABSTRACT

A guide wire includes a long flexible wire main body, and a coil that is formed by winding a plurality of wires in a spiral shape, and which is disposed at an outer periphery of a distal portion of the wire main body to cover the distal portion. The coil includes a coil distal portion that is disposed on a distal side in the distal portion, a coil proximal portion that is disposed on a further proximal side in comparison to the coil distal portion, and a coil intermediate portion that is disposed between the coil distal portion and the coil proximal portion, and includes a wire having a wire diameter that is smaller than a wire diameter of the wires of the coil distal portion and the coil proximal portion.

12 Claims, 9 Drawing Sheets

GUIDE WIRE

CROSS-REFERENCE TO RELATED APPLICATION

This application claims priority to Japanese Application Number 2016-225474 filed on Nov. 18, 2016, the entire content of which is incorporated herein by reference.

TECHNICAL FIELD

The present invention relates to a guide wire, and more particularly, to a guide wire that is used to introduce a catheter into a biological lumen such as a blood vessel and a bile duct.

BACKGROUND ART

By way of example, a guide wire is used when guiding a catheter used for treatment of a site in which it is difficult to perform a surgical operation, such as percutaneous transluminal coronary angioplasty (PTCA), a treatment which is aimed to be less invasive into the human body, or used in tests such as cardioangiography. The guide wire that is used for PTCA is inserted into the vicinity of a coronary artery stenosed site that is a target site in combination with a balloon catheter in a state in which a distal end of the guide wire protrudes from a distal end of the balloon catheter, and guides the distal portion of the balloon catheter into the vicinity of a blood vessel stenosed site.

In addition, even in a case of percutaneous transluminal angioplasty (PTA), the guide wire guides the balloon catheter to a stenosed site in the same manner as in PTCA so as to recanalize a stenosed and occluded site of a peripheral blood vessel such as, for example, a femoral, iliac, renal, or shunt.

In addition, in treatment of a lesion site of a bile duct or a pancreatic duct, the guide wire is used to guide each treatment device to the vicinity of the lesion site of the bile duct and the pancreatic duct, for example, in one of the following methods.

1. Endoscopic Retrograde Cholangiopancreatography (ERCP)

An X-ray photographing method in which an endoscope is inserted to a descending part of a duodenum, a contrast cannula is inserted into a bile duct or a pancreatic duct while viewing a vator papilla from a front side with the endoscope, and a contrast agent is injected.

2. Endoscopic Sphincterotomy (EST)

A method in which a cutting papillotome is inserted into a duodenal papilla opening, and a papilla sphincter muscle is cut with high-frequency waves.

3. Endoscopic Papillary Balloon Dilation (EPBD)

A method of removing a bile duct gallstone by expanding a papilla with a balloon through an endoscope.

A blood vessel for which PTCA is necessary is complicatedly curved. In addition, in PTCA with respect to a CTO lesion (completely occluded lesion) in which a part of a blood vessel is completely occluded due to calcification and the like, it is necessary to transfer a relatively strong thrusting-in force to a distal side of the guide wide. As described above, the blood vessel for which the PTCA is necessary is complicatedly curved, and in the PTCA with respect to the CTO lesion site, it is necessary to thrust in the guide wire with a relatively strong force. Therefore, there is a concern that blood vessel perforation, which is formed when the guide wire breaks through the blood vessel, may occur. According to this, the guide wire, which is used when inserting the balloon catheter into the blood vessel, is required to have flexibility and resilience with respect to appropriate bending, thrusting-in properties and torque transmission properties for transmission of an operation at a proximal portion to a distal side, kink resistance (bending resistance), and the like.

JP-A-2008-178656 discloses a guide wire provided with a coil including an increasing wire-diameter portion in which the wire diameter of the wire increases continuously or step by step in a distal direction. In addition, the coil described in JP-A-2008-178656 includes a constant wire-diameter portion in which the wire diameter of the wire is approximately constant. According to the guide wire described in JP-A-2008-178656, for example, when the guide wire is inserted into a catheter or a living body, a stress that occurs in the coil is mitigated in the increasing wire-diameter portion. Accordingly to this, the thrusting-in force is reliably transmitted to the distal end of the guide wire, and flexibility is obtained in the distal portion.

However, in the guide wire described in JP-A-2008-178656, when the guide wire reaches the occluded lesion and is thrust in, it is difficult to curve the guide wire to a desired position. Hence, with respect to the guide wire described in JP-A-2008-178656, there is room for improvement.

In addition, for example, in a case where the coil and a wire main body are fixed to each other with a fixing member, and a curved portion is formed, a diameter of the section in which the curved portion is formed increases. Accordingly, in a catheter or a living body in which an increased thrusting-in force is not necessary, there is a concern that passing-through properties may deteriorate.

SUMMARY

The disclosure herein provides a guide wire which is curved at a desired position when reaching an occluded lesion and being thrust in, and which has a curved portion that passes through the occluded lesion in a smooth manner. Thus, it is possible to suppress the occurrence of a blood vessel perforation in the occluded lesion when a thrusting-in force is necessary.

According to one aspect of the disclosure, there is provided a guide wire comprising: a long wire main body having flexibility; and a coil that is formed by winding wires in a spiral shape, and which is disposed at an outer periphery of a distal portion of the wire main body to cover the distal portion. The coil includes a coil distal portion that is disposed on a distal side in the distal portion, a coil proximal portion that is disposed further proximal in comparison to the coil distal portion, and a coil intermediate portion that is disposed between the coil distal portion and the coil proximal portion, and which includes a wire having a wire diameter that is smaller than a wire diameter of wires of the coil distal portion and the coil proximal portion.

According to this configuration, the coil, which is formed by winding the wires in a spiral shape, is disposed at the outer periphery of the distal portion of the flexible long wire main body so as to cover the distal portion of the wire main body. The coil includes the coil distal portion that is disposed on the distal side in the distal portion of the wire main body, the coil proximal portion that is disposed further proximal in comparison to the coil distal portion, and the coil intermediate portion that is disposed between the coil distal portion and the coil proximal portion. In addition, the wire diameter of the wire of the coil intermediate portion is smaller than the wire diameter of the wires of the coil distal portion and the coil proximal portion. Accordingly, when the guide wire reaches an occluded lesion and is thrust in, the coil intermediate portion becomes the origin of a curving in the guide wire. As a result, when the guide wire reaches the occluded lesion and is thrust in, it is possible to curve the guide wire at a desired position.

In the guide wire that is curved at the coil intermediate portion, a curved portion passes through the occluded lesion in a smooth manner. Accordingly, even when the curved portion of the guide wire reaches a blood vessel wall, a thrusting-in force that is transmitted from the guide wire to the blood vessel wall is dispersed. According to this, occurrence of blood vessel perforation is suppressed. In addition, when the guide wire reaches the occluded lesion and is thrust in, the coil intermediate portion becomes the origin of the curving. As a result, in a catheter or a living body for which an increased thrusting-in force is not necessary, deterioration of passing-through properties of the guide wire is suppressed.

According to a further aspect of the disclosure, the wire main body may include a small-diameter portion having an outer diameter that is smaller than an outer diameter of other portions, and the coil intermediate portion may be provided at a position that overlaps the small-diameter portion in a direction along a longitudinal direction of the wire main body.

According to such a configuration, the wire main body includes the small-diameter portion having an outer diameter smaller than that of other portions. In addition, the coil intermediate portion is provided at a position that overlaps the small-diameter portion in a direction along a longitudinal direction of the wire main body. That is, the coil intermediate portion is provided at a position that overlaps the small-diameter portion to which a stress is concentrated when the guide wire is thrust in. Accordingly, when the guide wire reaches the occluded lesion and is thrust in, the coil intermediate portion is likely to be the origin of curving in the guide wire. That is, the guide wire is likely to be curved at the coil intermediate portion.

According to a further aspect of the disclosure, the wire main body may include a tapered portion of which an outer diameter is gradually reduced toward a distal direction, and which is disposed further proximal in comparison to the small-diameter portion and is connected to the small-diameter portion, and the coil intermediate portion may be provided at a position that overlaps a portion in which the tapered portion is connected to the small-diameter portion in a direction along the axis.

According to such a configuration, the wire main body includes the tapered portion of which an outer diameter is gradually reduced toward the distal direction. The tapered portion is disposed on the proximal side relative to the small-diameter portion and is connected to the small-diameter portion. That is, the tapered portion is connected to the small-diameter portion on the distal side. In addition, the coil intermediate portion is provided at a position that overlaps a portion in which the tapered portion is connected to the small-diameter portion in a direction along the axis of the wire main body. That is, the coil intermediate portion is provided at a position that overlaps a portion in which the tapered portion and the small-diameter portion are connected to each other and at which a stress is concentrated when the guide wire is thrust in. Accordingly, when the guide wire reaches an occluded lesion and is thrust in, the coil intermediate portion is likely to be the origin of curving in the guide wire. That is, the guide wire is likely to be curved at the coil intermediate portion provided at a position that overlaps the connection portion between the tapered portion and the small-diameter portion.

According to a further aspect of the disclosure, the wire main body may include a flat plate portion that is formed in a flat plate shape, is disposed on a further distal side in comparison to the small-diameter portion, and is connected to the small-diameter portion, and the coil intermediate portion may be provided at a position that overlaps a portion in which the small-diameter portion is connected to the flat plate portion in a direction along the axis.

According to this configuration, the wire main body includes the flat plate portion that is formed in a flat plate shape. The flat plate portion is disposed further distal in comparison to the small-diameter portion and is connected to the small-diameter portion. That is, the flat plate portion is connected to the small-diameter portion on the proximal side. In addition, the coil intermediate portion is provided at a position that overlaps a portion in which the small-diameter portion is connected to the flat plate portion in a direction along the axis of the wire main body. That is, the coil intermediate portion is provided at a position that overlaps a portion in which the small-diameter portion and the flat plate portion are connected to each other and to which a stress is concentrated when the guide wire is thrust in. Accordingly, when the guide wire reaches an occluded lesion and is thrust-in, the coil intermediate portion is likely to be the origin of curving in the guide wire. That is, the guide wire is likely to be curved at the coil intermediate portion that is provided a position that overlaps the connection portion between the small-diameter portion and the flat plate portion. In addition, the flat plate portion is disposed on a further distal side in comparison to the small-diameter portion. Accordingly, it is possible to perform reshaping in an easy and reliable manner, and thus operability is significantly improved when the guide wire is inserted into a catheter or a living body.

According to a further aspect of the disclosure, the wire main body may include a small-diameter portion having an outer diameter that is smaller than an outer diameter of other portions, and a tapered portion of which an outer diameter is gradually reduced toward a distal direction, and which is disposed further proximal in comparison to the small-diameter portion, and the coil intermediate portion may be provided at a position that overlaps a proximal portion of the tapered portion in a direction along a longitudinal direction of the wire main body.

According to this configuration, the coil intermediate portion is provided at a position that overlaps the proximal portion of the tapered portion in a direction along a longitudinal direction of the wire main body. Since the coil intermediate portion is disposed at a position that overlaps the proximal portion of the tapered portion that is disposed on a further proximal side in comparison to the small-diameter portion, the guide wire is likely to be curved at a portion to which a stress is concentrated when the guide wire is thrust in. The outer diameter of the proximal portion of the tapered portion is greater than the outer diameter of the small-diameter portion and the outer diameter of the distal portion of the tapered portion. Accordingly, occurrence of blood vessel perforation is suppressed, and a thrusting-in force is reliably transmitted to the distal end of the guide wire.

According to a further aspect of the disclosure, the outer diameter of the coil distal portion may be smaller than an outer diameter of the coil proximal portion.

According to this configuration, the outer diameter of the coil distal portion is smaller than the outer diameter of the coil proximal portion, and thus properties of passing through an occluded lesion are improved. In addition, even in a case where the wire main body includes the small-diameter portion or the tapered portion, a space (clearance) between an inner surface of the coil and the wire main body is maintained constant. Accordingly, the thrusting-in force is reliably transmitted to the distal end of the guide wire, and when the guide wire reaches an occluded lesion and is thrust in, it is possible to curve the guide wire at a desired position.

According to a further aspect of the disclosure, the outer diameter of the coil intermediate portion may be the same as an outer diameter of the coil proximal portion and an outer diameter of the coil distal portion.

According to this configuration, since the outer diameter of the coil intermediate portion is the same as an outer diameter of the coil proximal portion and an outer diameter of the coil distal portion, a smooth coil surface is realized. Accordingly, for example, the coil is suppressed from being hooked or caught on a blood vessel wall, a catheter, and the like.

According to a further aspect of the disclosure, the inner diameter of the coil intermediate portion may be the same as an inner diameter of the coil proximal portion and an inner diameter of the coil distal portion.

According to this configuration, since the inner diameter of the coil intermediate portion is the same as the inner diameter of the coil proximal portion and the inner diameter of the coil distal portion, a space (clearance) between the inner surface of the coil and the wire main body is maintained in an approximately constant manner, and the outer diameter of the coil intermediate portion becomes smaller than the outer diameter of the coil proximal portion and the outer diameter of the coil distal portion. Accordingly, the thrusting-in force is reliably transmitted to the distal end of the guide wire, and when the guide wire reaches an occluded lesion and is thrust in, it is possible to allow the guide wire to be easily curved at a desired position.

Still further, according to a further aspect of the disclosure, a line, which connects centers in transverse cross-sections of the wires adjacent to each other, may be parallel to the axis.

According to this configuration, since the line, which connects centers in the transverse cross-sections of the wires adjacent to each other, is parallel to the axis of the wire main body, the adjacent wires are suppressed from being stranded. According to this, the thrusting-in force is reliably transmitted to the distal end of the guide wire.

According to the disclosure herein, it is therefore possible to provide a guide wire which is curved at a desired position when reaching an occluded lesion and thrust in, and in which a curved portion passes through the occluded lesion in a smooth manner, and thus it is possible to suppress occurrence of blood vessel perforation in the occluded lesion when a thrusting-in force is necessary.

DETAILED DESCRIPTION

Figure 1:
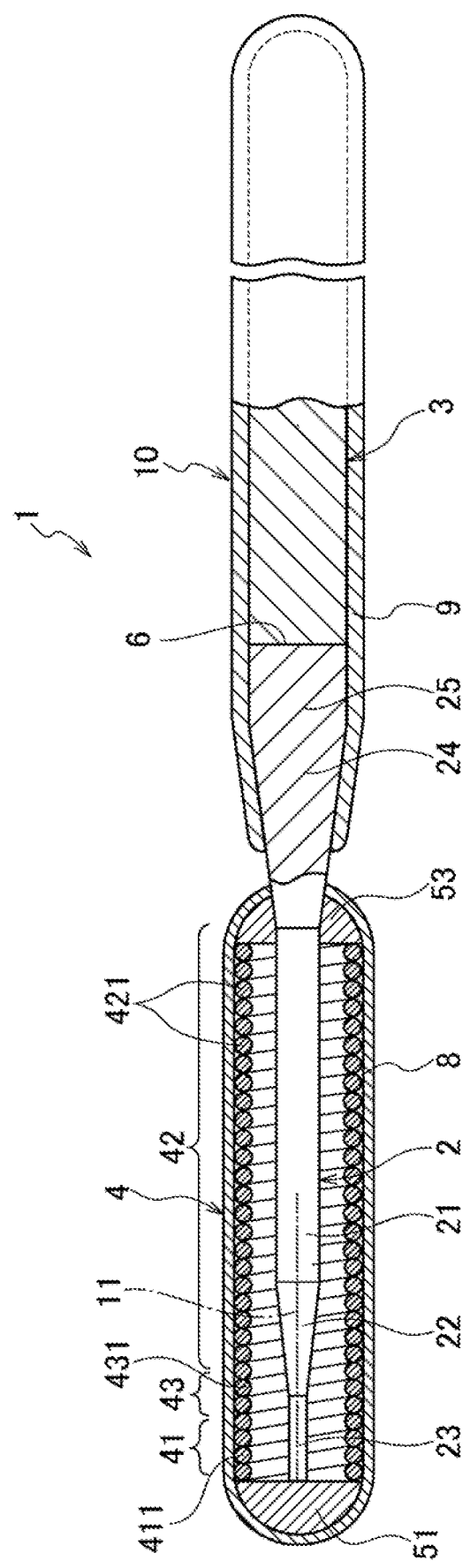
FIG. 1 is a cross-sectional view illustrating a guide wire according to a first exemplary embodiment of the disclosure.

Preferred exemplary embodiments of the disclosure herein will be described in detail with reference to the accompanying drawings.

Furthermore, exemplary embodiments to be described below are preferred specific examples, and various limitations that are technically preferable but not absolute are included. The present disclosure is thus not limited to these specific exemplary embodiments. In addition, in the drawings, the same reference numeral will be given to the same constituent element, and detailed description thereof will be appropriately omitted.

FIG. 1 is a cross-sectional view illustrating a guide wire according to a first exemplary embodiment of the disclosure herein.

Figure 2:
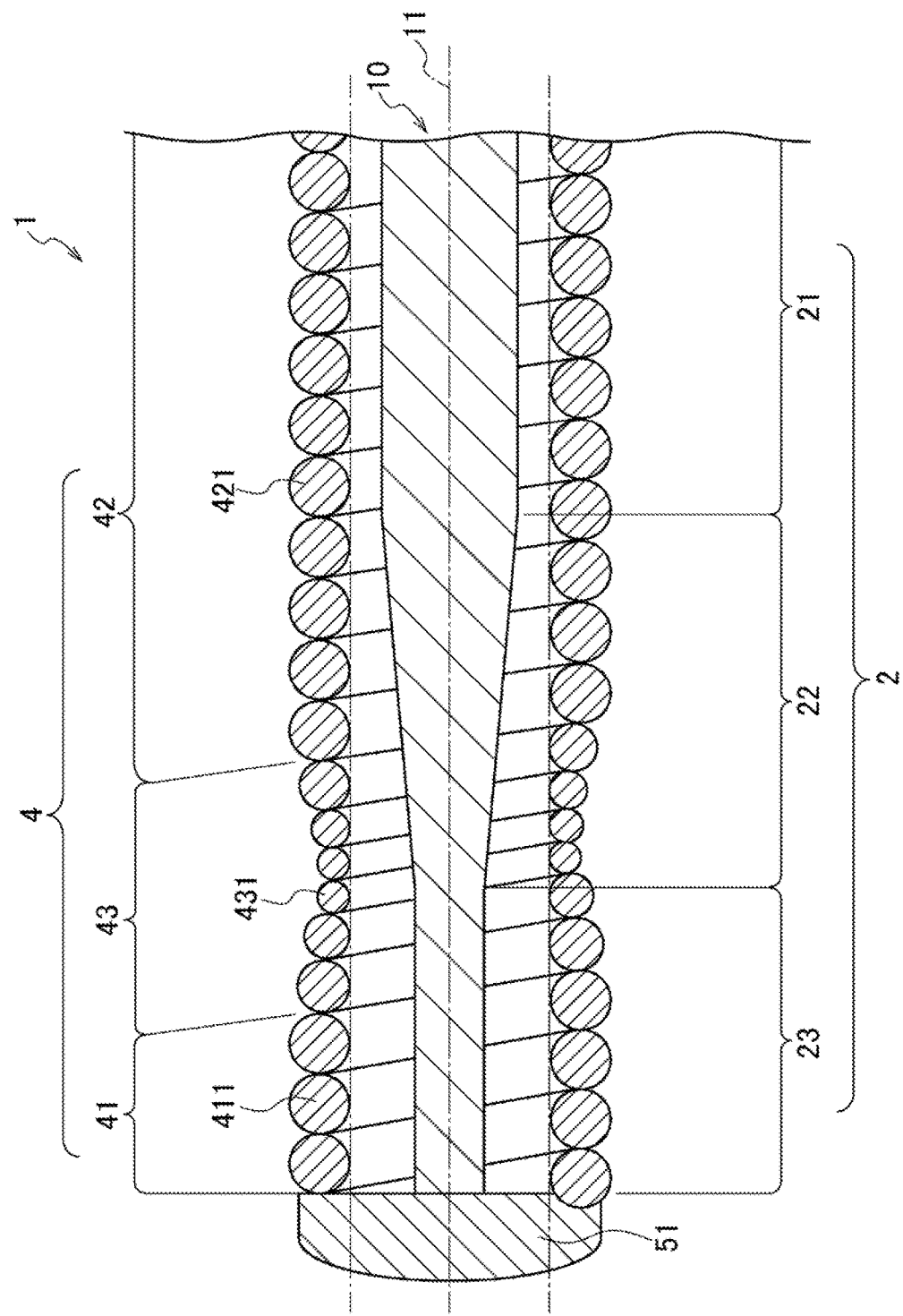
FIG. 2 is an enlarged view illustrating a distal portion of the guide wire according to the first exemplary embodiment in an enlarged manner.

FIG. 2 is an enlarged view illustrating a distal portion of the guide wire according to the first exemplary embodiment in an enlarged manner.

Furthermore, for convenience of explanation, in FIG. 1 and FIG. 2, a right side is referred to as "proximal end", and a left side is referred to as "distal end". In addition, in FIG. 1 and FIG. 2, a longitudinal direction of the guide wire is shortened, and a thickness direction of the guide wire is exaggeratedly and schematically illustrated for easy comprehension. That is, a ratio between the longitudinal direction and the thickness direction may be different from an actual ratio. In addition, in FIG. 2, a resin coating layer is omitted. These are also true of FIG. 4, FIG. 5, and FIG. 7 to FIG. 9.

A guide wire 1 illustrated in FIG. 1 is a guide wire for a catheter (also including an endoscope) which is used in a state of being inserted into a lumen of the catheter, and includes a wire main body 10, and a spiral coil 4 that is provided at a distal portion of the wire main body 10. The guide wire 1 may be used in combination with a catheter for passing through a coronary artery to improve passing-through properties at a bent portion or a stenosed site of a blood vessel, or to improve selectivity of a blood vessel at a bifurcated portion of a blood vessel. The wire main body 10 is a long wire having flexibility, and includes a first wire 2 that is disposed on a distal side, and a second wire 3 that is disposed on a proximal side of the first wire 2. Preferably, the first wire 2 and the second wire 3 are bonded (connected) through welding. Although not particularly limited, for example, the total length of the guide wire 1 is preferably approximately 200 to 5000 mm.

The first wire 2 is formed from a wire rod having flexibility or elasticity. Although not particularly limited, for example, the length of the first wire 2 is preferably approximately 20 to 1000 mm.

In this exemplary embodiment, the first wire 2 includes a first constant-diameter portion (large-diameter portion) 21, a second constant-diameter portion (small-diameter portion) 23, a first tapered portion (tapered portion) 22, a second tapered portion 24, and a third constant-diameter portion 25. The first constant-diameter portion 21 corresponds to a large-diameter portion of the disclosure. The second constant-diameter portion 23 corresponds to a small-diameter portion of the disclosure. The first tapered portion 22 corresponds to a tapered portion of the disclosure. An outer diameter (diameter) of the first constant-diameter portion 21 is approximately constant. The second constant-diameter portion 23 is located on a further distal side of the guide wire in comparison to the first constant-diameter portion 21. An outer diameter (diameter) of the second constant-diameter portion 23 is smaller than the outer diameter of the first constant-diameter portion 21 and is approximately constant. The first tapered portion 22 is located between the first constant-diameter portion 21 and the second constant-diameter portion 23. An outer diameter (diameter) of the first tapered portion 22 is gradually reduced toward a distal direction. The third constant-diameter portion 25 is located on a further proximal side of the guide wire in comparison to the first constant-diameter portion 21. An outer diameter (diameter) of the third constant-diameter portion 25 is greater than the outer diameter of the first constant-diameter portion 21, and is approximately constant. The second tapered portion 24 is located between the first constant-diameter portion 21 and the third constant-diameter portion 25. An outer diameter (diameter) of the second tapered portion 24 is gradually reduced toward the distal direction. The third constant-diameter portion 25, the second tapered portion 24, the first constant-diameter portion 21, the first tapered portion 22, and the second constant-diameter portion 23 are disposed in this order from the proximal side of the first wire 2 toward the distal side thereof. That is, the first tapered portion 22 is disposed on a further proximal side in comparison to the second constant-diameter portion 23, and is connected to the second constant-diameter portion 23.

The second constant-diameter portion 23 and the first constant-diameter portion 21 are formed with the first tapered portion 22 interposed therebetween. The first constant-diameter portion 21 and the third constant-diameter portion 25 are formed with the second tapered portion 24 interposed therebetween. With this arrangement, it is possible to gradually reduce the rigidity (bending rigidity, torsional rigidity) of the first wire 2 toward the distal direction. As a result, the guide wire 1 obtains satisfactory properties of passing through a stenosed site and satisfactory flexibility at a distal portion thereof. Further, follow-up properties to a blood vessel and the like and safety are improved, and bending resistance and the like can be prevented.

A taper angle (outer diameter reduction rate) of the first tapered portion 22 and the second tapered portion 24 may be constant along a longitudinal direction of the wire main body 10, or may vary along the longitudinal direction. For example, a portion in which the taper angle is relatively great and a portion in which the taper angle is relatively small may be formed in a repetitively alternating manner a plurality of times.

An outer diameter of a proximal-side portion (that is, the third constant-diameter portion 25) of the first wire 2 is made to be constant up to the proximal end of the first wire 2. A length of the first constant-diameter portion 21 is preferably shorter than a length of a coil proximal portion 42 to be described later. A length between the distalmost end of the guide wire 1 and a proximal portion of the first tapered portion 22 (a boundary portion between the first tapered portion 22 and the first constant-diameter portion 21) is not particularly limited, but it is preferable that the length is approximately 5 to 200 mm, and more preferably 10 to 150 mm.

Preferably, a distal end of the second wire 3 is connected (linked) to the proximal end of the first wire 2 (proximal end of the third constant-diameter portion 25) through welding. That is, the second wire 3 is connected (linked) to the first wire 2 at a joint portion (joint surface) 6. The second wire 3 is formed from a wire rod having flexibility or elasticity.

Although not particularly limited, examples of a method of welding the first wire 2 and the second wire 3 include friction pressure welding, spot welding using a laser, butt resistance welding such as butt seam welding and upset welding, and the like. Among these, the butt resistance welding is more preferable when considering high joining strength in a relatively simple manner.

In this exemplary embodiment, the outer diameter (diameter) of the second wire 3 is approximately constant along a longitudinal direction thereof.

The outer diameter of the second wire 3 is approximately the same as the outer diameter of the third constant-diameter portion 25 of the first wire 2. Hence, when a proximal end of the third constant-diameter portion 25 of the first wire 2 and the distal end of the second wire 3 are joined, hardly any step difference due to a difference in an outer diameter between the first wire 2 and the second wire 3 occurs at an outer periphery of the joint portion 6. Thus, at the joint portion 6 between the first wire 2 and the second wire 3, a continuous surface is constructed.

The second wire 3 has an outer diameter that is greater than the outer diameter of the first constant-diameter portion 21 of the first wire 2. For example, the outer diameter of the second wire 3 is approximately 1.02 to 5 times the outer diameter of the first constant-diameter portion 21 of the first wire 2.

Although not particularly limited, the length of the second wire 3 is preferably approximately 20 to 4800 mm, and more preferably approximately 1400 to 3000 mm.

An average outer diameter of the first wire 2 is smaller than an average outer diameter of the second wire 3. Accordingly, the guide wire 1 has a highly flexible property at the first wire 2 that is disposed on a distal side and a relatively high rigid property at the second wire 3 that is disposed on a proximal side. As such, in the guide wire 1, the flexibility of the distal portion and excellent operability (thrust-in properties, torque transmission properties, and the like) are compatible with each other.

Although not particularly limited, examples of materials for the first wire 2 and the second wire 3 include various metal materials such as stainless steel (for example, all kinds of SUS such as SUS304, SUS303, SUS316, SUS316L, SUS316J1, SUS316J1L, SUS405, SUS430, SUS434, SUS444, SUS429, SUS430F, and SUS302), a piano wire, a cobalt-based alloy, an alloy (including a super-elastic alloy) that exhibits pseudo-elasticity, and the like. Among these, as the material of the first wire 2 and the second wire 3, the alloy (including the super-elastic alloy) that exhibits pseudo-elasticity is particularly preferable, and the super-elastic alloy is more preferable.

The super-elastic alloy is relatively flexible, and has resilience, and thus has a property in which a bending curl caused by permanent deformation is less likely to occur. Accordingly, when the super-elastic alloy is used as a material of the first wire 2, the guide wire 1 can obtain sufficient flexibility at a distal-side portion and resilience against bending. In addition, follow-up properties with respect to a blood vessel, which is complicatedly curved and bent, and the like are improved, and thus excellent operability can be obtained with respect to the guide wire 1. Even when the first wire 2 is repetitively subjected to curving and bending deformation, the bending curl does not occur due to the resilience provided to the first wire 2, and thus deterioration of the operability due to occurrence of the bending curl in the first wire 2 during use of the guide wire 1 is prevented.

The pseudo-elastic alloy includes any shape of a stress-strain curve due to tension, and examples of the pseudo-elastic alloy include alloys in which transformation temperatures such as As, Af, Ms, and Mf can be significantly measured and alloys in which the transformation temperatures cannot be significantly measured. In addition, examples of the pseudo-elastic alloy include alloys which are greatly deformed (distorted) due to a stress, and return to the original shape due to removal of the stress.

Examples of a preferred composition of the super-elastic alloy include a Ni—Ti-based alloy such as an Ni—Ti alloy containing 49 to 52 at % of Ni, a Cu—Zn alloy containing 38.5 to 41.5 weight % of Zn, a Cu—Zn—X alloy containing 1 to 10 weight % of X (X represents at least one kind among Be, Si, Sn, Al, and Ga), a Ni—Al alloy containing 36 to 38 at % of Al, and the like. Among these, the Ni—Ti-based alloy is more preferable. Furthermore, the super-elastic alloy, which is represented by the Ni—Ti-based alloy is excellent in adhesiveness with a resin coating layer (8, 9) to be described later.

When being used as a wire, the cobalt-based alloy has a high elastic modulus, and has an appropriate elastic limit. Accordingly, in a wire constituted by the cobalt-based alloy, torque transmission properties are excellent, and a problem such as buckling is less likely to occur. The cobalt-based alloy may be any alloy as long as the alloy contains Co as a constituent element. However, an alloy (a Co base alloy: an alloy in which among elements which constitute the alloy, a content rate of Co is the greatest in terms of a weight ratio) that contains Co as a main component is preferable, and a Co—Ni—Cr-based alloy is more preferable. When using the alloy having the above-described composition, the above-described effect becomes more significant. In addition, the alloy having the above-described composition has a high elastic coefficient, cold molding thereof is possible even in a high elastic limit, and it has a high elastic limit. Accordingly, occurrence of buckling in a wire is sufficiently prevented, and a reduction in a diameter of the wire is possible. In addition, with regard to insertion into a predetermined portion, the wire can have sufficient flexibility and rigidity.

Preferred examples of the Co—Ni—Cr-based alloy include an alloy having a composition of 28 to 50 wt % of Co—, 10 to 30 wt % of Ni—, 10 to 30 wt % of Cr—, and the remainder including Fe, an alloy obtained by substituting a part of the alloy with another element (substituent element), and the like. When containing the substituent element, a unique effect corresponding to a kind thereof is exhibited. For example, as the substituent element, at least one kind selected from Ti, Nb, Ta, Be, and Mo is included, a further improvement in the strength of the second wire 3, and the like are realized. Furthermore, in a case where elements other than Co, Ni, and Cr are included, it is preferable that the entire amount of the substituent elements is 30 wt % or less.

In addition, a part of Co, Ni, and Cr may be substituted with other elements. For example, a part of Ni may be substituted with Mn. Accordingly, for example, a further improvement of workability, and the like are realized. In addition, a part of Cr may be substituted with Mo and/or W. Accordingly, a further improvement of an elastic limit, and the like are realized. It is more preferable that the cobalt-based alloy is a Co—Ni—Cr—Mo-based alloy including Mo among Co—Ni—Cr-based alloys.

Examples of a specific composition of the Co—Ni—Cr-based alloy include (1) 40 wt % of Co—, 22 wt % of Ni—, 25 wt % of Cr—, 2 wt % of Mn—, 0.17 wt % of C—, 0.03 wt % of Be—, and the remainder including Fe, (2) 40 wt % of Co—, 15 wt % of Ni—, 20 wt % of Cr—, 2 wt % of Mn—, 7 wt % of Mo—, 0.15 wt % of C—, 0.03 wt % of Be—, and the remainder including Fe, (3) 42 wt % of Co—, 13 wt % of Ni—, 20 wt % of Cr—, 1.6 wt % of Mn—, 2 wt % of Mo—, 2.8 wt % of W—, 0.2 wt % of C—, 0.04 wt % of Be—, and the remainder including Fe, (4) 45 wt % of Co—, 21 wt % of Ni—, 18 wt % of Cr—, 1 wt % of Mn—, 4 wt % of Mo—, 1 wt % of Ti—, 0.02 wt % of C—, 0.3 wt % of Be—, and the remainder including Fe, (5) 34 wt % of Co—, 21 wt % of Ni—, 14 wt % of Cr—, 0.5 wt % of Mn—, 6 wt % of Mo—, 2.5 wt % of Nb—, 0.5 wt % of Ta—, and the remainder including Fe, and the like. The Co—Ni—Cr-based alloy stated in the disclosure here is intended to include the above-described alloys.

The first wire 2 and the second wire 3 may be constituted by materials different from each other, or may be constituted by the same or the same kind of metal material. Here, "the same kind" is understood to mean that a main metal material in an alloy is the same as each other. Accordingly, the joining strength at the joint portion 6 further increases, and even in a case where an outer diameter of the joint portion 6 is small, the likelihood of detachment of the first wire 2 and the second wire 3 occurring is reduced. Accordingly, excellent torque transmission properties and the like are exhibited.

It is preferable that the first wire 2 and the second wire 3 are constituted by the above-described super-elastic alloys, and more preferably the Ni—Ti-based alloy among the alloys. As such, excellent flexibility is secured on the distal side of the wire main body 10, and sufficient rigidity (bending rigidity, torsional rigidity) is secured at a proximal-side portion of the wire main body 10. As a result, in the guide wire 1, excellent thrusting-in properties and excellent torque transmission properties are obtained, and thus satisfactory operability is secured. In addition, satisfactory flexibility and resilience are obtained on the distal side, and thus follow-up properties to a blood vessel, a bile duct, and a pancreatic duct, and safety can be improved.

In a case where the first wire 2 and the second wire 3 are constituted by materials different from each other, it is preferable that the first wire 2 is constituted by the above-described super-elastic alloy, particularly, the Ni—Ti-based alloy. It is preferable that the second wire 3 is constituted by the above-described stainless steel.

In addition, the first wire 2 and the second wire 3 may be constituted by pseudo-elastic alloys or two kinds of stainless steel different in a metal composition or physical properties.

Furthermore, description has been given with reference to an aspect of the disclosure in which the first wire 2 and the second wire 3 are joined to each other as an example, but the wire main body 10 may be one member of wire without the joint portion. Examples of the constituent material of the wire in this case include the same materials as described above. Particularly, as the constituent material of the wire the stainless steel, the cobalt-based alloy, and the pseudo-elastic alloy are preferable.

The coil 4 is disposed at the outer periphery of the distal portion of the wire main body 10 to cover the distal portion of the wire main body 10. When the coil 4 is provided, a contact area between a surface of the wire main body 10 relative to an inner wall of a catheter or a surface of a living body decreases. As such, sliding resistance is reduced and the operability of the guide wire 1 is further improved.

The coil 4 includes a coil distal portion 41 that is located on the distal side, a coil proximal portion 42 that is disposed on a further proximal side in comparison to the coil distal portion 41, and a coil intermediate portion 43 that is disposed between the coil distal portion 41 and the coil proximal portion 42.

The coil distal portion 41 is a member obtained by winding a wire (fine wire) 411 into a spiral shape, and is provided to cover at least a distal-side portion of the first wire 2. In the guide wire 1 illustrated in FIG. 1 and FIG. 2, the distal-side portion of the first wire 2 is disposed at an approximately center portion of an inner side of the coil distal portion 41. In addition, the distal-side portion of the first wire 2 is disposed in a state such that it does not come into contact with an inner surface of the coil distal portion 41. That is, the coil distal portion 41 covers at least the distal-side portion of the first wire 2 in a state where it is separated from the first wire 2 (in a state of not coming into contact with the first wire 2).

The coil proximal portion 42 is a member obtained by winding a wire (fine wire) 421 in a spiral shape, and is provided to cover a distal-side portion of the first wire 2 which is a portion on a further proximal side in comparison to the coil distal portion 41. In the guide wire 1 illustrated in FIG. 1 and FIG. 2, the distal-side portion of the first wire 2 is disposed at an approximately central portion on an inner side of the coil proximal portion 42. In addition, the distal-side portion of the first wire 2 is disposed in a state such that it does not come into contact with an inner surface of the coil proximal portion 42. That is, the coil proximal portion 42 covers at least the distal-side portion of the first wire 2 in a state where it is separated from the first wire 2 (in a state of not coming into contact with the first wire 2).

The coil intermediate portion 43 is a member that is obtained by winding a wire (fine wire) 431 in a spiral shape, and is disposed to cover a portion of the first wire 2 between the coil distal portion 41 and the coil proximal portion 42. In the guide wire 1 illustrated in FIG. 1 and FIG. 2, the portion of the first wire 2, which is covered with the coil intermediate portion 43, is disposed at an approximately central portion on an inner side of the coil intermediate portion 43. In addition, the portion of the first wire 2, which is covered with the coil intermediate portion 43, is disposed in a state such that it does not come into contact with an inner surface of the coil intermediate portion 43. That is, the coil intermediate portion 43 covers a portion of the first wire 2 that is located between the coil distal portion 41 and the coil proximal portion 42 in a state where it is separated from the first wire 2 (in a state of not coming into contact with the first wire 2).

As illustrated in FIG. 2, the coil intermediate portion 43 is provided at a position that overlaps the second constant-diameter portion 23 in a direction along the axis 11 in the longitudinal direction of the wire main body 10. In addition, the coil intermediate portion 43 is provided at a position that overlaps a portion (a boundary portion between the first tapered portion 22 and the second constant-diameter portion 23) in which the first tapered portion 22 is connected to the second constant-diameter portion 23 in direction along the axis 11 of the wire main body 10. That is, the coil intermediate portion 43 of this exemplary embodiment is disposed to cover the vicinity of a boundary portion between the first tapered portion 22 and the second constant-diameter portion 23.

An outer diameter (coil outer diameter) of the coil 4 is approximately constant along a longitudinal direction except for the coil intermediate portion 43. In this specification, "outer diameter (coil outer diameter) of a coil" is understood to mean an outer diameter of the entirety of the coil obtained by winding a wire in a spiral shape instead of a wire outer diameter (wire diameter) of the coil. That is, the outer diameter of the coil distal portion 41 and the outer diameter of the coil proximal portion 42 are approximately constant along a longitudinal direction thereof. In addition, the outer diameter of the coil intermediate portion 43 is smaller than the outer diameter of the coil proximal portion 42 and the outer diameter of the coil distal portion 41.

The maximum outer diameter Dmax of the coil 4 is preferably approximately 0.25 to 0.89 mm, and more preferably approximately 0.25 to 0.46 mm. The minimum outer diameter Dmin of the coil 4 is preferably approximately 0.10 to 0.86 mm, and more preferably approximately 0.15 to 0.38 mm. In addition, a ratio Dmin/Dmax between the maximum outer diameter Dmax and the minimum outer diameter Dmin is approximately 0.3 to 0.95, and more preferably approximately 0.44 to 0.83. When the maximum outer diameter Dmax and the minimum outer diameter Dmin are in these ranges, the above-described effect is more significantly exhibited. In addition, it is preferable that the maximum outer diameter Dmax of the coil 4 is approximately the same as the diameter of the second wire 3.

Although not particularly limited, a total length (L0) of the coil 4 is preferably approximately 5 to 500 mm, and more preferably approximately 30 to 300 mm. In addition, when a length of the coil proximal portion 42 is set as L1, L1/L0 is preferably 0.05 to 0.9. In addition, it is preferable that a position, at which the coil intermediate portion 43 is provided, is spaced from the distalmost end of the guide wire 1 toward the proximal end, for example, by approximately 1 to 3 mm.

A wire diameter (diameter) of the wire 411 in the coil distal portion 41 is approximately the same as a wire diameter (diameter) of the wire 421 in the coil proximal portion 42. On the other hand, a wire diameter (diameter) of the wire 431 in the coil intermediate portion 43 is smaller than the wire diameter of the wire 411 in the coil distal portion 41 and the wire diameter of the wire 421 in the coil proximal portion 42. As illustrated in FIG. 2, the wire diameter of the wire 431 in the coil intermediate portion 43 is gradually reduced from the coil distal portion 41 side and the coil proximal portion 42 side toward the central portion of the coil intermediate portion 43.

The maximum diameter dmax of the wires 411, 421, and 431 is preferably approximately 0.23 to 0.87 mm, and more preferably approximately 0.23 to 0.44 mm. In this exemplary embodiment, the maximum diameter dmax represents a wire diameter of at least one of the wire 411 in the coil distal portion 41 and the wire 421 in the coil proximal portion 42. The minimum diameter dmin of the wires 411, 421, and 431 is preferably approximately 0.06 to 0.20 mm, and more preferably 0.08 to 0.15 mm. In this exemplary embodiment, the minimum diameter dmin is a wire diameter of the wire 431 in the coil intermediate portion 43. In addition, a ratio dmin/dmax between the maximum diameter dmax and the minimum diameter dmin is preferably approximately 0.1 to 0.9, and more preferably approximately 0.18 to 0.44. When the maximum diameter dmax and the minimum diameter dmin are in the ranges, the above-described effect is more significantly exhibited in combination with the conditions of the minimum outer diameter Dmin and the maximum outer diameter Dmax.

In this first exemplary embodiment, shapes of the wire 411, the wire 421, and the wire 431 in the transverse cross-section are circles, respectively, but there is no limitation to the circle. For example, the shape of at least one of the wire 411, the wire 421, and the wire 431 in the transverse cross-section may be an ellipse, a square (particularly, a rectangle), and the like. In the disclosure here, "transverse cross-section of a wire" is understood to mean a cut end (cut-out surface) when being cut out along a plane perpendicular to an axis that extends in a longitudinal direction of the wire.

In addition, in the coil distal portion 41, the coil proximal portion 42, and the coil intermediate portion 43 of the guide wire 1 illustrated in FIG. 1, wires wound in a spiral shape are closely disposed without a gap in a state in which an external force is not applied, but a slight gap may be present between the wires differently from the illustrated embodiment.

A constituent material of the coil distal portion 41 (wire 411), the coil proximal portion 42 (wire 421), and the coil intermediate portion 43 (wire 431) may be any one of a metal material and a resin material. However, it is preferable that at least the wire 421 among the wire 411, the wire 421, and the wire 431 is constituted by the metal material, and it is more preferable that the entirety of the wire 411, the wire 421, and the wire 431 are constituted by the metal material.

Examples of the metal material that constitutes the wire 411, the wire 421, and the wire 431 include the same materials exemplified as the constituent material of the first wire 2 and the second wire 3. In addition, examples of other metals include a cobalt-based alloy, a noble metal such as gold, platinum, and tungsten, alloys (for example, a platinum-iridium alloy) containing these materials, and the like. Particularly, in a case where the wire 411, the wire 421, and the wire 431 are constituted by a radiopaque material such as the noble metal, radiopacity is obtained at the distal portion of the guide wire 1. Accordingly, an operator can insert the guide wire 1 into a living body while confirming a position of the distal portion under X-ray fluoroscopy.

In addition, the coil distal portion 41 (wire 411), the coil proximal portion 42 (wire 421), and the coil intermediate portion 43 (wire 431) may be constituted by materials different from each other. Preferred examples thereof include a case where the wire 411 and the wire 431 are constituted by a super-elastic alloy such as a Ni—Ti alloy, and the wire 421 is constituted by stainless steel. In this case, the torque transmission properties and the thrusting-in properties in the coil 4 are secured, and more flexible properties are obtained on the distal side of the coil 4. Other examples in which the coil distal portion 41, the coil proximal portion 42, and the coil intermediate portion 43 are constituted by materials different from each other include a case where the wire 411 and the wire 431 are constituted by a radiopaque material, and the wire 421 is constituted by a material (stainless steel and the like) through which an X-ray is relatively transmitted.

In a case where the entirety of the coil distal portion 41 (wire 41), the coil proximal portion 42 (wire 421), and the coil intermediate portion 43 (wire 431) do not have radiopacity, a marker having radiopacity may be additionally provided. An example thereof is a configuration in which a filler formed from the radiopaque material is dispersed in the resin coating layer 8 as to be described later.

The coil 4 illustrated in FIG. 1 is fixed to the wire main body 10 at two sites. That is, the distal portion of the coil distal portion 41 is fixed to the distal end of the first wire 2 by a fixing material (fixing portion) 51. The proximal portion of the coil proximal portion 42 is fixed to a portion (the vicinity of a boundary between the first constant-diameter portion 21 and the second tapered portion 24) partway through the first wire 2 by a fixing material (fixing portion) 53. When the coil 4 is fixed to the wire main body 10 at these positions, the coil distal portion 41 and the coil proximal portion 42 are reliably fixed without deteriorating flexibility of the distal portion (portion in which the coil 4 exists) of the guide wire 1.

Furthermore, the coil 4 may be fixed to the wire main body 10 at three sites. In this case, for example, the distal portion of the coil proximal portion 42 is fixed to a portion (for example, the vicinity of the proximal portion of the first tapered portion 22) partway through the first wire 2 by a fixing material (fixing portion). When the coil 4 is fixed to the wire main body 10 at three such positions, the coil distal portion 41 and the coil proximal portion 42 are reliably fixed without deteriorating flexibility of the distal portion (portion in which the coil 4 exists) of the guide wire 1.

The fixing materials 51 and 53 are composed of solder (brazing material). Furthermore, the fixing materials 51 and 53 may be an adhesive without limitation to the solder. In addition, examples of a method of fixing the coil 4 to the wire main body 10 include welding without limitation to the fixing by the fixing material as described above. In addition, it is preferable that a distal end surface of the fixing material 51 is rounded so as to prevent damage of an inner wall of a biological lumen such as a blood vessel.

As illustrated in FIG. 1, the wire main body 10 includes resin coating layers 8 and 9 as a coating layer that covers the entirety of a part of an outer peripheral surface (outer surface). In the embodiment illustrated in FIG. 1, the resin coating layer 8 is provided at an outer periphery of the coil 4. In addition, the resin coating layer 9 is provided at a part of the first wire 2 and an outer periphery of the second wire 3. Particularly, in the guide wire 1 illustrated in FIG. 1, the entirety or parts of the wire 411, the wire 421, and the wire 431 are provided in the resin coating layer 8.

The resin coating layers 8 and 9 are provided for various purposes. As an example, the resin coating layers 8 and 9 reduce friction (sliding resistance) of the guide wire 1, and improve sliding properties thereof. As a result, the resin coating layers 8 and 9 may improve the operability of the guide wire 1.

To realize the reduction in the friction (sliding resistance) of the guide wire 1, it is preferable that the resin coating layers 8 and 9 are constituted by a material capable of reducing friction as described below. Hence, frictional resistance (sliding resistance) between the guide wire 1 and an inner wall of a catheter that is used in combination with the guide wire 1 is reduced, and sliding properties are improved. As a result, the operability of the guide wire 1 in the catheter becomes more satisfactory. In addition, because the sliding resistance of the guide wire 1 is reduced, when the guide wire 1 moves and/or rotates in the catheter, kink (bending) or twisting of the guide wire 1, particularly, kink or twisting in the vicinity of the joint portion 6 is more reliably prevented.

Examples of a material capable of reducing the friction include polyolefin such as polyethylene and polypropylene, polyvinyl chloride, polyester (PET, PBT, and the like), polyamide, polyimide, polyurethane, polystyrene, polycarbonate, a silicone resin, a fluorine-based resin (PTFE, ETFE, and the like), and composite materials thereof.

Among the materials, particularly, in a case where the fluorine-based resin (or a composite material that includes the fluorine-based resin) is used, frictional resistance (sliding resistance) between the guide wire 1 and the inner wall of the catheter is more effectively reduced, and sliding properties are improved. As a result, the operability of the guide wire 1 in the catheter becomes more satisfactory. In addition, when the guide wire 1 moves and/or rotates in the catheter, kink (bending) or twisting of the guide wire 1, particularly, kink or twisting in the vicinity of welded portion can be more reliably prevented.

In addition, in a case where the fluorine-based resin (or a composite material including the fluorine-based resin) is used, the wire main body 10 is coated with the fluorine-based resin in a state in which the resin material is heated in accordance with a method such as baking and spraying. Accordingly, the resin coating layers 8 and 9 have particularly excellent adhesiveness.

In addition, in a case where the silicone resin (or a composite material including the silicon resin) is used as the material of the resin coating layers 8 and 9, when the coil 4 and the wire main body 10 are coated with the resin coating layers 8 and 9, the resin coating layers 8 and 9, form reliable and strong contact with the wire main body 10 even when heating is not performed. That is, in a case where the silicone resin (or a composite material including the silicone resin) is used as the material of the resin coating layers 8 and 9, a reactive-curing material and the like can be used, and thus the resin coating layers 8 and 9 are formed at room temperature. In this manner, since the resin coating layers 8 and 9 are formed at room temperature, coating can be performed in a convenient manner, and the guide wire 1 can be operated in a state in which the joining strength between the first wire 2 and the second wire 3 at the joint portion 6 is sufficiently maintained.

In addition, as another example, the resin coating layers 8 and 9 (particularly, the resin coating layer 8 on the distal side) are provided for the purpose of improving safety when the guide wire 1 is inserted into a blood vessel and the like. To attain this purpose, it is preferable that the resin coating layers 8 and 9 are formed with a flexible material (a soft material or an elastic material).

Examples of the flexible material include polyolefin such as polyethylene and polypropylene, polyvinyl chloride, polyester (PET, PBT, and the like), polyamide, polyimide, polyurethane, polystyrene, a silicone resin, thermoplastic elastomers such as a polyurethane elastomer, a polyester elastomer, and a polyamide elastomer, various rubber materials such as a latex rubber and a silicone rubber, or composite materials in which two or more of the above-described materials are combined.

Particularly, in a case where the thermoplastic elastomers or the various rubber materials are used as the material of the resin coating layers 8 and 9, the flexibility of the distal portion of the guide wire 1 is further improved. Hence, a blood vessel inner wall and the like are more reliably prevented from being damaged by insertion of the guide wire into the blood vessel and the like, and thus safety greatly increases.

Each of the resin coating layers 8 and 9 may be a laminated body of two or more layers. In addition, the resin coating layer 8 and the resin coating layer 9 may be formed from the same material or materials different from each other. For example, the resin coating layer 8, which is located on the distal side of the guide wire 1, is formed from the above-described flexible material (a soft material or an elastic material). In addition, the resin coating layer 9, which is located on the proximal side of the guide wire 1, is formed from the above-described material capable of reducing friction. Accordingly, an improvement of slidability (operability) and an improvement of safety are compatible with each other.

The thickness of the resin coating layers 8 and 9 is not particularly limited, and is suitably set in consideration of the purpose of forming the resin coating layers 8 and 9 and a constituent material thereof, a forming method, and the like. Typically, the thickness (average thickness) of the resin coating layers 8 and 9 is preferably approximately 1 to 100 μm, and more preferably approximately 1 to 30 μm. When the thickness of the resin coating layers 8 and 9 is excessively small, the purpose of forming the resin coating layers 8 and 9 may not be sufficiently exhibited, and there is a concern that peeling-off of the resin coating layers 8 and 9 may occur. On the other hand, when the thickness of the resin coating layers 8 and 9 is excessively large, there is a concern that physical properties of the guide wire 1 may be affected, and peeling-off of the resin coating layers 8 and 9 may occur.

Furthermore, in an exemplary embodiment, a treatment (rough surface processing, a chemical treatment, a heat treatment, and the like) for improving adhesiveness of the resin coating layers 8 and 9 may be performed with respect to an outer peripheral surface (surface) of the coil 4 or the wire main body 10, or an intermediate layer capable of improving the adhesiveness of the resin coating layers 8 and 9 may be provided on the outer peripheral surface.

It is preferable that the resin coating layer 8 covers the distalmost end (including the fixing material 51) of the coil 4 without exposure, and the distal end of the resin coating layer 8 has a rounded shape. As such, when the guide wire 1 is inserted into a biological lumen such as a blood vessel, an inner wall of the biological lumen is more effectively prevented from being damaged, and thus safety increases.

In addition, a filler (particles) formed from a material having radiopacity (a radiopaque material and the like) may be dispersed in the resin coating layer 8. A radiopaque portion is thereby formed in the resin coating layer 8.

It is preferable that an outer surface of at least the distal portion of the guide wire 1 is coated with a hydrophilic material. In the exemplary embodiment, the outer peripheral surface of the guide wire 1 is coated with the hydrophilic material in a range from the distal end of the guide wire 1 to the vicinity of the proximal end of the second tapered portion 24. The hydrophilic material thus increases the lubricity of the guide wire. In addition, friction (sliding resistance) of the guide wire 1 is reduced, and thus sliding properties are improved. Accordingly, the operability of the guide wire 1 is improved. Furthermore, the resin coating layer 8 may be provided as a coating layer for generation of the lubricity.

Examples of the hydrophilic material include a cellulose-based polymer substance, a polyethylene oxide-based polymer substance, a maleic anhydride-based polymer substance (for example, a maleic anhydride copolymer such as methyl vinyl ether-maleic anhydride copolymer), an acrylamide-based polymer substance (for example, polyacrylamide, block copolymer of polyglycidyl methacrylate-dimethyl acrylamide (PGMA-DMAA)), water-soluble nylon, polyvinyl alcohol, polyvinyl pyrrolidone, and the like.

In many cases, the hydrophilic material exhibits lubricity due to wetting (water absorption), and reduces frictional resistance (sliding resistance) between the guide wire 1 and an inner wall of a catheter that is used in combination with the guide wire 1. Sliding properties of the guide wire 1 are thus improved and the operability of the guide wire 1 in the catheter becomes more satisfactory.

Figure 3A:
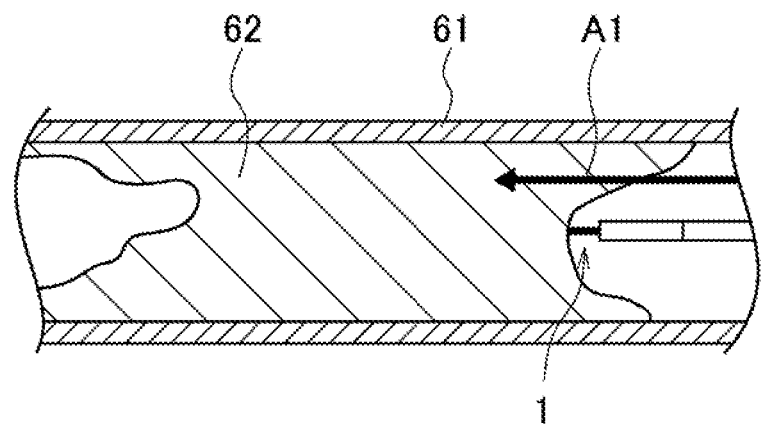
FIG. 3(A) and FIG. 3(B) are cross-sectional views each illustrating a state in which the guide wire according to the first exemplary embodiment passes through a CTO lesion.
Figure 3B:
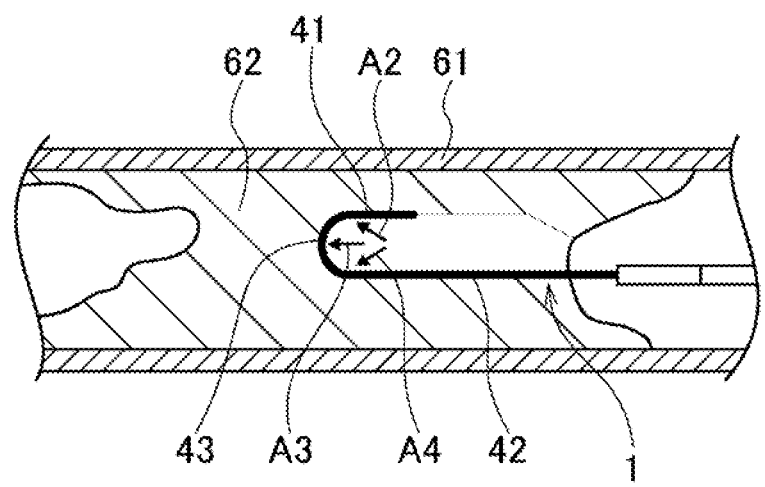

FIGS. 3(A) and 3(B) are cross-sectional views illustrating a state in which the guide wire according to the first exemplary embodiment passes through a CTO lesion.

FIG. 3(A) is a cross-sectional view illustrating a state in which the distal end of the guide wire reaches the CTO lesion. FIG. 3(B) is a cross-sectional view illustrating a state in which a curved portion of the guide wire passes through the CTO lesion in a smooth manner. Furthermore, FIGS. 3(A) and 3(B) illustrate an example in which the guide wire according to the exemplary embodiment is used in combination with a catheter for passing through a coronary artery.

For example, the guide wire 1 according to the first exemplary embodiment is used to guide a catheter that is used for a treatment of a site in which it is difficult to perform a surgical operation, such as percutaneous transluminal coronary angioplasty (PTCA), a treatment which is aimed at being minimally invasive into the human body, or a test such as cardioangiography. A blood vessel for which the PTCA is necessary is complicated and is curved. In addition, in the PTCA with respect to a CTO lesion (completely occluded lesion) in which a part of a blood vessel is completely occluded due to calcification and the like, it is necessary to transfer a relatively strong thrusting-in force to a distal side of the guide wide. As described above, the blood vessel for which the PTCA is necessary is complicatedly curved, and in the PTCA with respect to the CTO lesion site, it is necessary to thrust in the guide wire with a relatively strong force. Therefore, there is a concern that blood vessel perforation, which is formed when the guide wire breaks through the blood vessel, may occur.

In contrast, in the guide wire 1 according to the exemplary embodiment, the wire diameter of the wire 431 in the coil intermediate portion 43 is smaller than the wire diameter of the wire 411 in the coil distal portion 41 and the wire diameter of the wire 421 in the coil proximal portion 42. Accordingly, when the guide wire 1 reaches a CTO lesion 62 and is thrust in as indicated by an arrow A1 illustrated in FIG. 3(A), the coil intermediate portion 43 becomes the origin of curving in the guide wire 1 as illustrated in FIG. 3(B). Accordingly, it is possible to curve the guide wire 1 at a position that is intended in advance (a predetermined position). That is, when the guide wire 1 reaches the CTO lesion 62, it is possible to curve the guide wire 1 at a desired position within the CTO.

As illustrated in FIG. 3(B), in the guide wire 1 that is curved at the coil intermediate portion 43, a curved portion passes through the CTO lesion 62 in a smooth manner. Accordingly, even when the curved portion of the guide wire 1 reaches a blood vessel wall 61, the thrusting-in force, which is transmitted from the guide wire 1 to the blood vessel wall 61, is dispersed (refer to an arrow A2, an arrow A3, and an arrow A4 illustrated in FIG. 3(B)). Thus, occurrence of blood vessel perforation is suppressed. In addition, when the guide wire 1 reaches the CTO lesion 62 and is thrust in, the coil intermediate portion 43 becomes the origin of the curving. Accordingly, in a catheter or a living body for which the increased thrusting-in force is not necessary, deterioration of passing-through properties of the guide wire 1 is suppressed. That is, in a catheter or a living body for which the increased thrusting-in force is not necessary, the guide wire 1 according to the exemplary embodiment shows an approximately linear shape as illustrated in FIG. 1 and FIG. 2.

In addition, the coil intermediate portion 43 is provided at a position that overlaps the second constant-diameter portion 23 in a direction along the longitudinal axis 11 of the wire main body 10. That is, the outer diameter of the second constant-diameter portion 23 is smaller than the outer diameter of the first constant-diameter portion 21. Accordingly, the coil intermediate portion 43 is provided at the position that overlaps the second constant-diameter portion 23 to which a stress is concentrated when the guide wire 1 is thrust in. Accordingly, when the guide wire 1 reaches the CTO lesion 62 and is thrust in, the coil intermediate portion 43 is likely to become the origin of curving in the guide wire 1. That is, the guide wire 1 is likely to be curved at the coil intermediate portion 43.

In addition, the coil intermediate portion 43 is provided at a position that overlaps a portion (a boundary portion between the first tapered portion 22 and the second constant-diameter portion 23) in which the first tapered portion 22 is connected to the second constant-diameter portion 23 in a direction along the axis 11 of the wire main body 10. That is, the coil intermediate portion 43 is disposed to cover the vicinity of the boundary portion between the first tapered portion 22 and the second constant-diameter portion 23. That is, the coil intermediate portion 43 is provided at a position that overlaps a portion in which the first tapered portion 22 and the second constant-diameter portion 23 are connected to each other and to which a stress is concentrated when the guide wire 1 is thrust in. Accordingly, when the guide wire 1 reaches the CTO lesion 62 and is thrust in, the coil intermediate portion 43 is likely to become the origin of curving in the guide wire 1. That is, the guide wire 1 is likely to be curved at the coil intermediate portion 43 that is provided at a position that overlaps a portion in which the first tapered portion 22 and the second constant-diameter portion 23 are connected to each other. Hence, when the guide wire 1 reaches the CTO lesion 62, it is possible to curve the guide wire 1 at a desired position, and thus occurrence of blood vessel perforation is suppressed.

In addition, the inner diameter (coil inner diameter) of the coil intermediate portion 43 is the same as the inner diameter (coil inner diameter) of the coil distal portion 41, and the inner diameter (coil inner diameter) of the coil proximal portion 42. Accordingly, a space (clearance) between an inner surface of the coil 4 and the wire main body 10 is maintained in an approximately constant manner. Accordingly, the thrusting-in force is reliably transmitted to the distal end of the guide wire 1, and it is possible to allow the guide wire 1 to be easily curved at a desired position.

In addition, as described above, the outer diameter of the coil intermediate portion 43 is smaller than the outer diameter of the coil proximal portion 42 and the outer diameter of the coil distal portion 41. Specifically, the wire diameter of the wire 431 in the coil intermediate portion 43 is gradually reduced from the coil distal portion 41 side and the coil proximal portion 42 side toward the central portion of the coil intermediate portion 43. Accordingly, the guide wire 1 is likely to be curved at the central portion of the coil intermediate portion 43, and a curved portion passes through the CTO lesion 62 in a smooth manner. Relatively satisfactory passing-through properties of the guide wire 1 are thereby obtained. In addition, a step difference is suppressed from occurring at a boundary portion between the coil intermediate portion 43 and the coil distal portion 41, and a boundary portion between the coil intermediate portion 43 and the coil proximal portion 42. Accordingly, a smooth coil surface is realized over the coil distal portion 41, the coil intermediate portion 43, and the coil proximal portion 42. Thus, for example, the coil 4 is suppressed from being hooked or caught on a blood vessel, a catheter, and the like.

Furthermore, in the exemplary embodiment, as illustrated in FIG. 2, description has been given of a case where the coil intermediate portion 43 is provided at a position that overlaps a portion in which the first tapered portion 22 and the second constant-diameter portion 23 are connected to each other in a direction along the longitudinal axis 11 of the wire main body 10 as an example. However, positioning of the coil intermediate portion 43 is not limited thereto. For example, as described later with reference to FIG. 8, the coil intermediate portion 43 may be provided at a position that overlaps the proximal portion of the first tapered portion 22 in a direction along the longitudinal axis 11 of the wire main body 10. Alternatively, as described later with reference to FIG. 9, the coil intermediate portion 43 may be provided at a position that overlaps a portion in which the second constant-diameter portion 23 is connected to a flat plate portion 26 in a direction along the longitudinal axis 11 of the wire main body 10. Details thereof will be described later.

Figure 4:
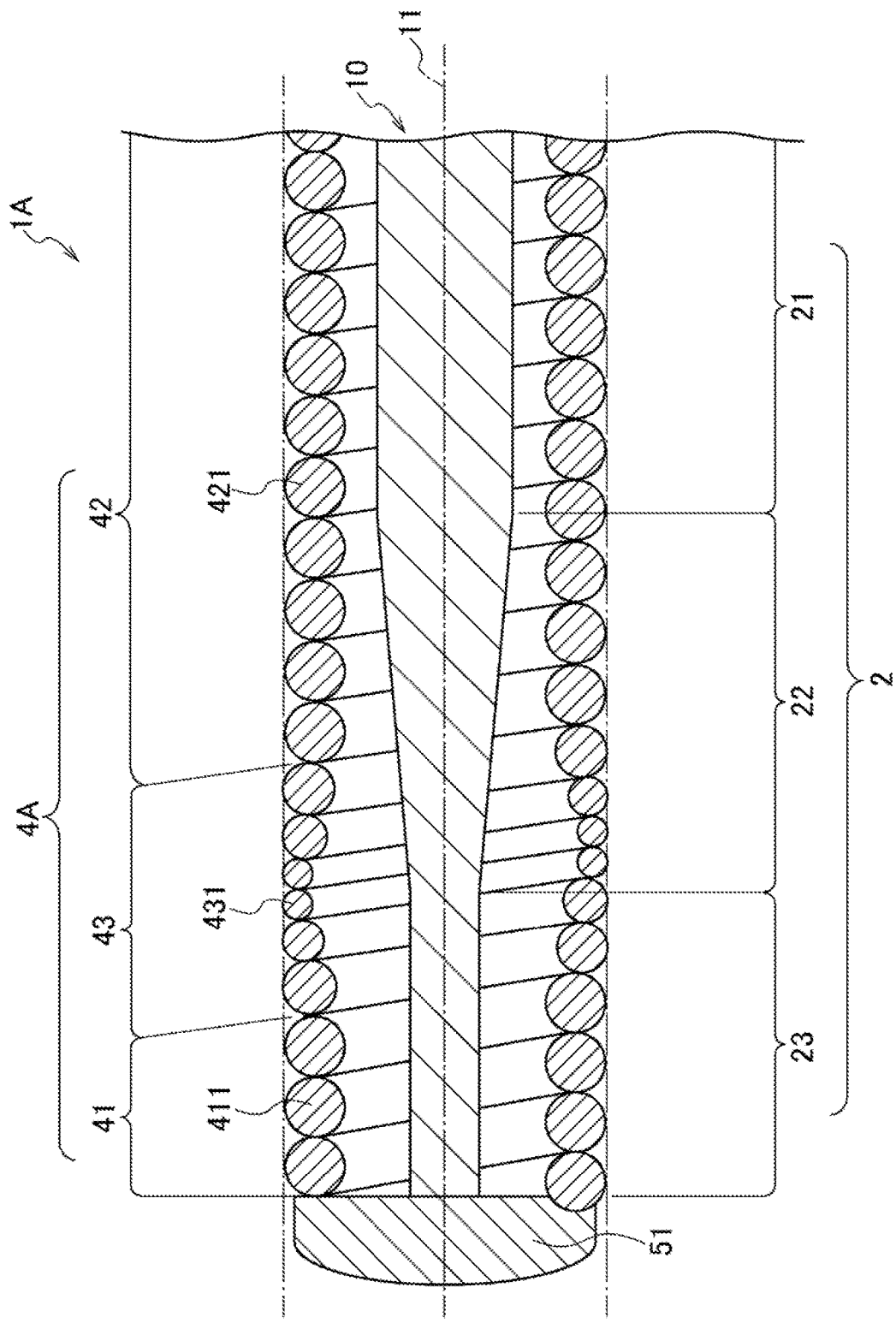
FIG. 4 is a cross-sectional view illustrating a guide wire according to a first modified example of the first exemplary embodiment.

FIG. 4 is a cross-sectional view illustrating a guide wire according to a first modified example of the first embodiment.

Similar to FIG. 2, FIG. 4 corresponds to an enlarged view illustrating the distal portion of the guide wire according to the modified example in an enlarged manner.

In a guide wire 1A according to the first modified example, an outer diameter (coil outer diameter) of a coil 4A is approximately constant along a longitudinal direction. That is, an outer diameter of a coil distal portion 41, an outer diameter of a coil proximal portion 42, and an outer diameter of a coil intermediate portion 43 are approximately constant along the longitudinal direction. In addition, the outer diameter of the coil intermediate portion 43 is the same as the outer diameter of the coil proximal portion 42 and the outer diameter of the coil distal portion 41. With respect to this configuration, the guide wire 1A according to this modified example is different from the guide wire 1 described above with reference to FIG. 1 and FIG. 2. The other structures are the same as in the guide wire 1 described above with reference to FIG. 1 and FIG. 2.

According to the guide wire 1A according to this modified example, the outer diameter of the coil intermediate portion 43 is the same as the outer diameter of the coil proximal portion 42 and the outer diameter of the coil distal portion 41, and thus a smooth coil surface is realized. Hence, for example, the coil 4A is suppressed from being hooked or caught on a blood vessel wall, a catheter, and the like. In addition, the same effect described above with reference to FIG. 1 to FIG. 3(B) is obtained.

Figure 5:
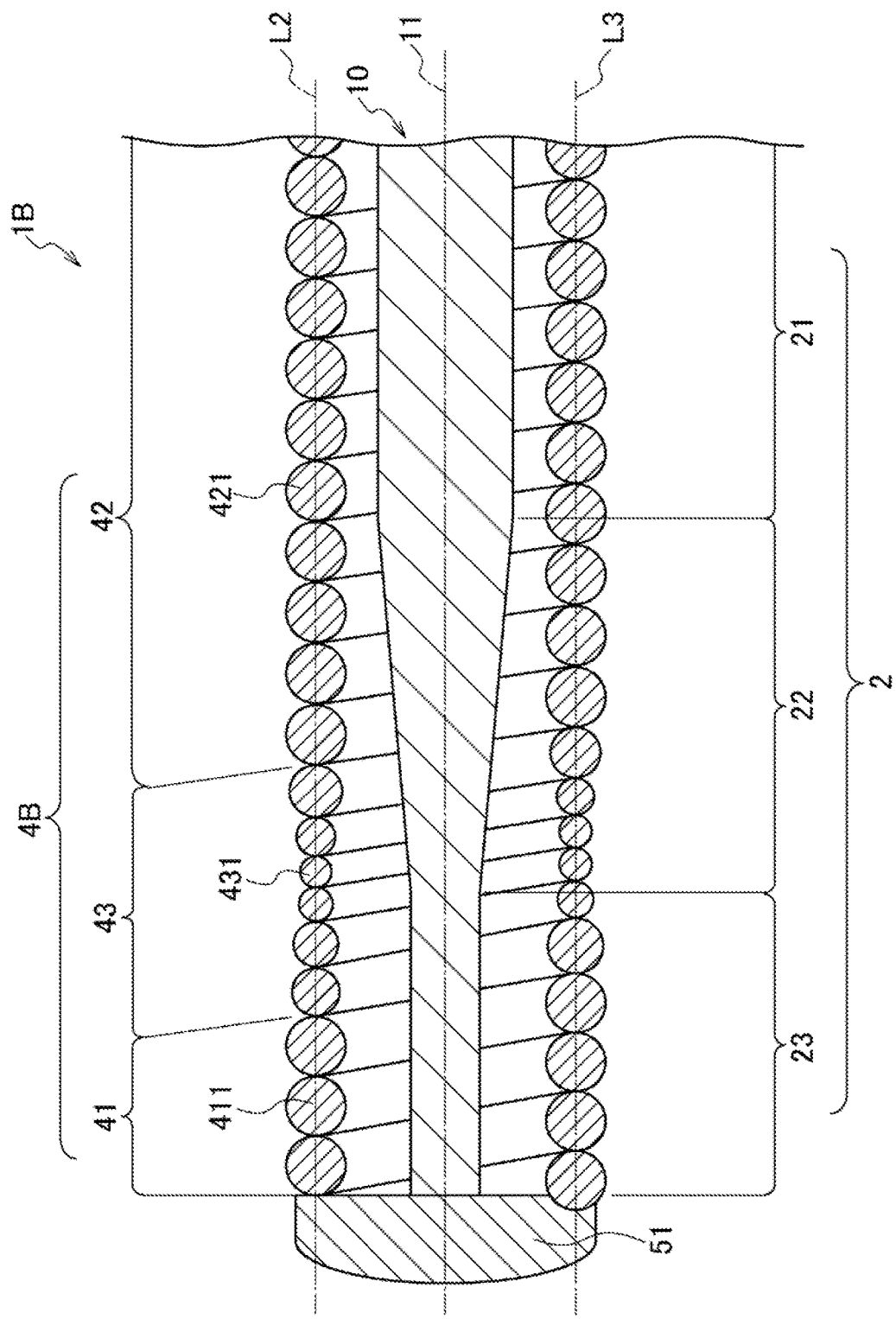
FIG. 5 is a cross-sectional view illustrating a guide wire according to a second modified example of the first exemplary embodiment.

FIG. 5 is a cross-sectional view illustrating a guide wire according to a second modified example of the first exemplary embodiment.

Similar to FIG. 4, FIG. 5 corresponds to an enlarged view illustrating a distal portion of the guide wire according to this modified example in an enlarged manner.

In a coil 4B of a guide wire 1B according to the second modified example, lines (L2 and L3), which connect the centers in transverse cross-sections of wires 411, 421, and 431 adjacent to each other, are parallel to an axis 11 of a wire main body 10. The other structures are the same as structure of the guide wire 1 described above with reference to FIG. 1 and FIG. 2.

According to this modified example, the wires 411, 421, and 431 adjacent to each other are suppressed from being moved upwards or downward relative to the adjacent wires because the force caused by pushing the guide wire is transmitted through the center lines of the wires. The thrusting-in force is thus reliably transmitted to a distal end of the guide wire 1B. In addition, the same effect described with reference to FIG. 1 to FIG. 3(B) is obtained.

Next, description will be given of a second exemplary embodiment of the disclosure.

Furthermore, in a case where constituent elements of a guide wire according to the second exemplary embodiment are the same as the constituent elements of the guide wires 1, 1A, and 1B according to the first exemplary embodiment described above with reference to FIG. 1 to FIG. 5, redundant description will be appropriately omitted, and description will be made with focus given to the differences in configuration.

Figure 6:
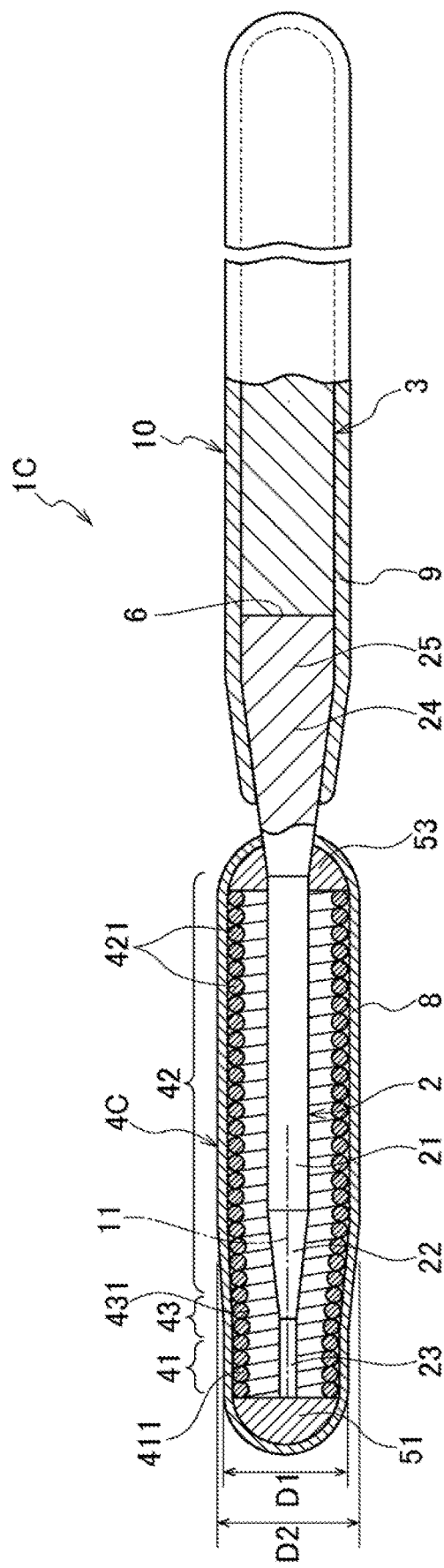
FIG. 6 is a cross-sectional view illustrating a guide wire according to a second exemplary embodiment of the disclosure.

FIG. 6 is a cross-sectional view illustrating a guide wire according to the second exemplary embodiment of the disclosure herein.

Figure 7:
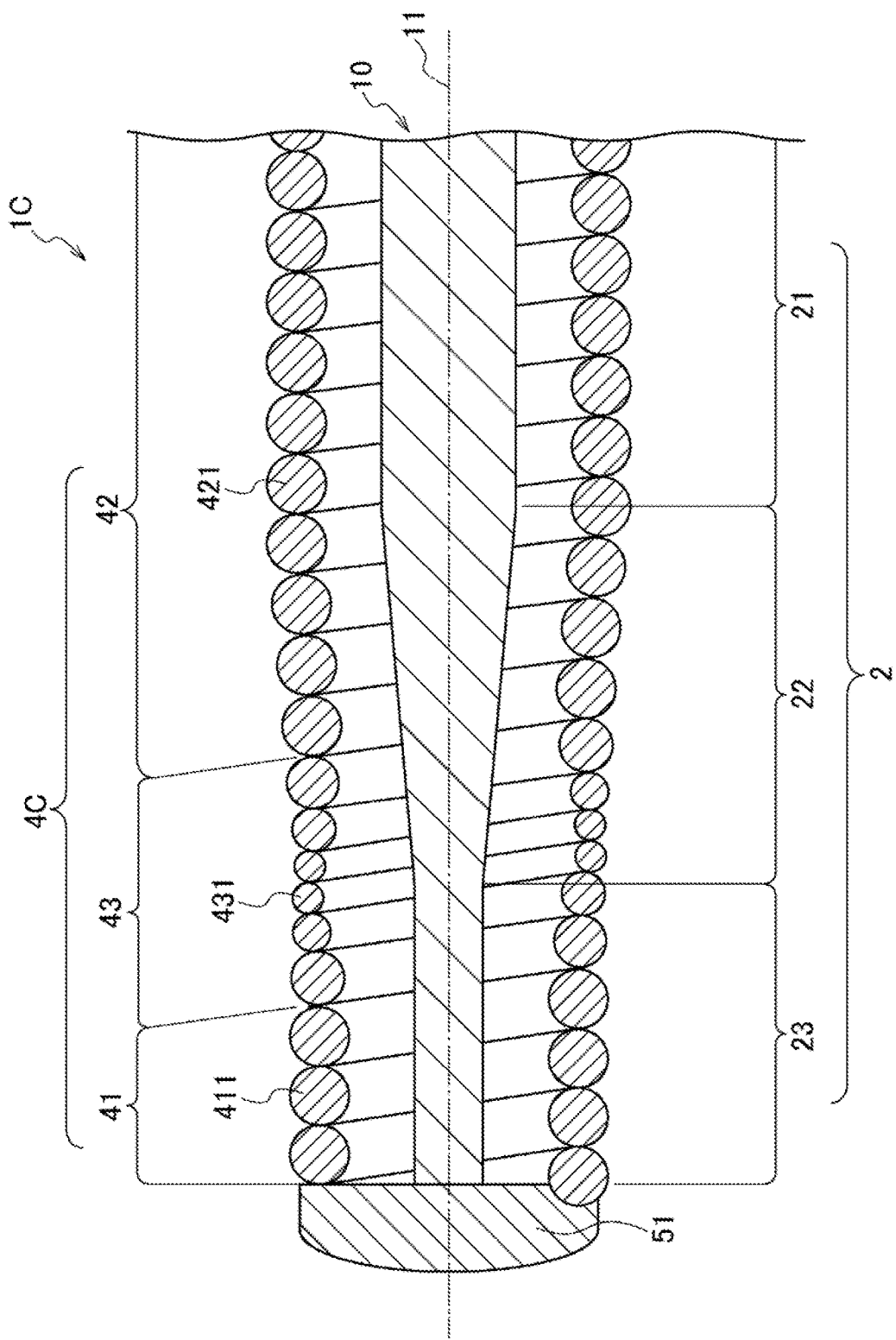
FIG. 7 is an enlarged view illustrating a distal portion of the guide wire according to the second exemplary embodiment in an enlarged manner.

FIG. 7 is an enlarged view illustrating a distal portion of the guide wire according to the second exemplary embodiment in an enlarged manner.

In a guide wire 1C according to the secondary exemplary embodiment, a coil 4C includes a portion in which an outer diameter (coil outer diameter) is gradually reduced toward the distal direction. Specifically, a coil distal portion 41 has a portion in which an outer diameter D1 is approximately constant along a longitudinal direction. In addition, a coil proximal portion 42 includes a portion in which an outer diameter D2 is approximately constant along the longitudinal direction. On the other hand, at least any of the coil distal portion 41, the coil proximal portion 42, and the coil intermediate portion 43 includes a portion in which the outer diameter is gradually reduced toward the distal direction. That is, a portion, in which the coil outer diameter is gradually reduced toward the distal direction, exists at least at any one of the coil distal portion 41, the coil proximal portion 42, and the coil intermediate portion 43.

Accordingly, as illustrated in FIG. 6, the outer diameter D1 of the coil distal portion 41 is smaller than the outer diameter D2 of the coil proximal portion 42. Along with the reduction in the outer diameter of the coil 4C, the outer diameter of the guide wire 1C is also gradually reduced toward the distal end. With respect to this point, the guide wire 1C according to the second exemplary embodiment is different from the guide wire 1 described above with reference to FIG. 1 and FIG. 2. The other structures are the same as in the guide wire 1 described above with reference to FIG. 1 and FIG. 2.

According to the guide wire 1C according to this second exemplary embodiment, in an operation of inserting the guide wire 1C into a living body (into a catheter), operability is improved. In addition, flexibility gradually increases due to the reduction in the outer diameter of the guide wire 1C, and stress concentration is prevented. Accordingly, kink resistance and safety are improved. In addition, the coil distal portion 41 includes a portion in which the outer diameter D1 is approximately constant along the longitudinal direction, and the coil proximal portion 42 includes a portion in which the outer diameter D2 is approximately constant along the longitudinal direction, and thus insertion resistance is further reduced when the guide wire 1C is inserted into the catheter or the living body.

In addition, the outer diameter D1 of the coil distal portion 41 is smaller than the outer diameter D2 of the coil proximal portion 42, and thus properties of passing-through the CTO lesion 62 are improved. Even in a case where the wire main body 10 includes the second constant-diameter portion 23 and the first tapered portion 22, a space (clearance) between in inner surface of the coil 4C and the wire main body 10 is maintained in an approximately constant manner. Thus, the thrusting-in force is reliably transmitted to the distal end of the guide wire 1C, and it is possible to curve the guide wire 1C at a desired position.

As illustrated in FIG. 7, a wire 431 in the coil intermediate portion 43 is disposed between a wire 411 in the coil distal portion 41 and a wire 421 in the coil proximal portion 42 in such a manner that an outer surface of the coil 4C becomes continuous. Accordingly, a smooth coil surface is realized and the coil 4C is suppressed from being hooked or caught on a blood vessel wall, a catheter, and the like.

Furthermore, the wire 431 in the coil intermediate portion 43 is disposed between the wire 411 in the coil distal portion 41 and the wire 421 in the coil proximal portion 42 in such a manner that an inner surface of the coil 4C becomes continuous. In this case, a space (clearance) between the inner surface of the coil 4C and the wire main body 10 is maintained in an approximately constant manner, and the outer diameter of the coil intermediate portion 43 becomes smaller than the outer diameter of the coil distal portion 41 and the outer diameter of the coil proximal portion 42. Hence, the thrusting-in force is reliably transmitted to the distal end of the guide wire 1C, and when the guide wire 1C reaches the CTO lesion 62 and is thrust in, it is possible to allow the guide wire 1C to be easily curved at a desired position.

Further, the wire 431 in the coil intermediate portion 43 may be disposed between the wire 411 in the coil distal portion 41 and the wire 421 in the coil proximal portion 42 so that a line, which connects the centers in transverse cross-sections of the wires 411, 421, and 431 adjacent to each other, becomes parallel to outer surface (a contour line) of the wire main body 10 in a longitudinal cross-section. In this specification, "a longitudinal cross-section of a wire main body" represents a cut end (cut-out surface) when being cut out along a plane on the longitudinal axis 11 of the wire main body 10. In this case, the wires 411, 421, and 431 adjacent to each other are suppressed from being stranded. The thrusting-in force is thereby reliably transmitted to the distal end of the guide wire 1C. In addition, the same effect described with reference to FIG. 1 to FIG. 3(B) is obtained.

Figure 8:
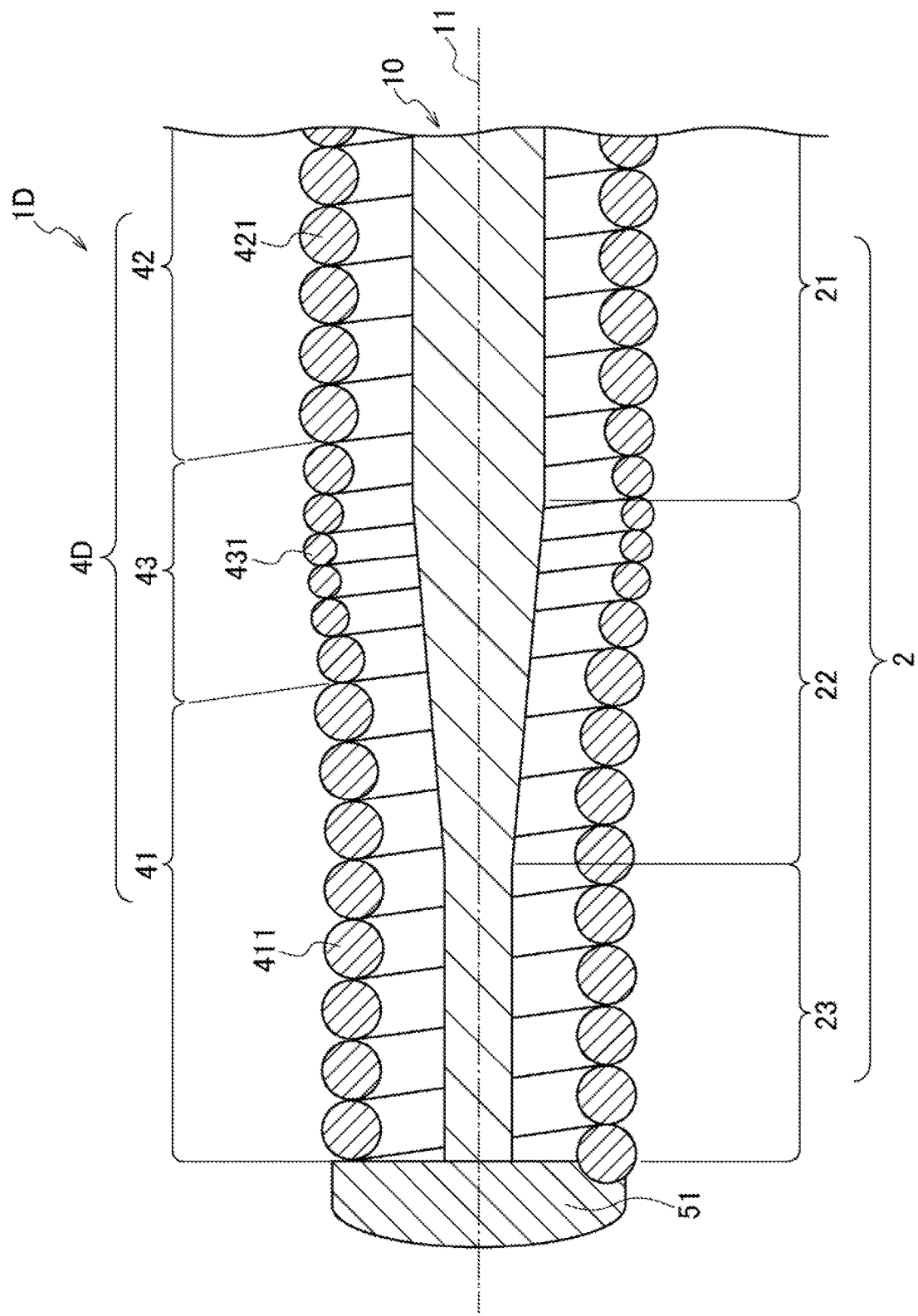
FIG. 8 is a cross-sectional view illustrating a guide wire according to a first modified example of the second exemplary embodiment.

FIG. 8 is a cross-sectional view illustrating a guide wire according to a first modified example of the second exemplary embodiment.

Similar to FIG. 7, FIG. 8 corresponds to an enlarged view illustrating a distal portion of the guide wire according to this modified example in an enlarged manner. In this modified example, as is the case with the guide wire 1C described above with reference to FIG. 6 and FIG. 7, description will be given of a case where a wire 431 in a coil intermediate portion 43 is disposed between a wire 411 in a coil distal portion 41 and a wire 421 in a coil proximal portion 42 in such a manner that an outer surface of a coil 4D becomes continuous as an example. This is also true of a second modified example to be described later with reference to FIG. 9.

In the guide wire 1D according to the first modified example, the coil intermediate portion 43 of the coil 4D is provided at a position that overlaps a proximal portion of a first tapered portion 22 in a direction along a longitudinal axis 11 of a wire main body 10. In addition, the coil intermediate portion 43 is provided at a position that overlaps a portion (a boundary portion between the first tapered portion 22 and the first constant-diameter portion 21) in which the first tapered portion 22 is connected to a first constant-diameter portion 21 in a direction along the axis 11 of the wire main body 10. That is, the coil intermediate portion 43 of this modified example is disposed to cover the vicinity of the boundary portion between the first tapered portion 22 and the first constant-diameter portion 21. The other structures are the same as the structures of the guide wire 1C described above with reference to FIG. 6 and FIG. 7.

According to this first modified example, the guide wire 1D is likely to be curved at a portion to which a stress is concentrated when the guide wire 1D is thrust in. An outer diameter of a proximal portion of the first tapered portion 22 is larger than an outer diameter of the second constant-diameter portion 23 and an outer diameter of a distal portion of the first tapered portion 22. Accordingly, occurrence of blood vessel perforation is suppressed, and the thrusting-in force is reliably transmitted to a distal end of the guide wire 1D.

Figure 9:
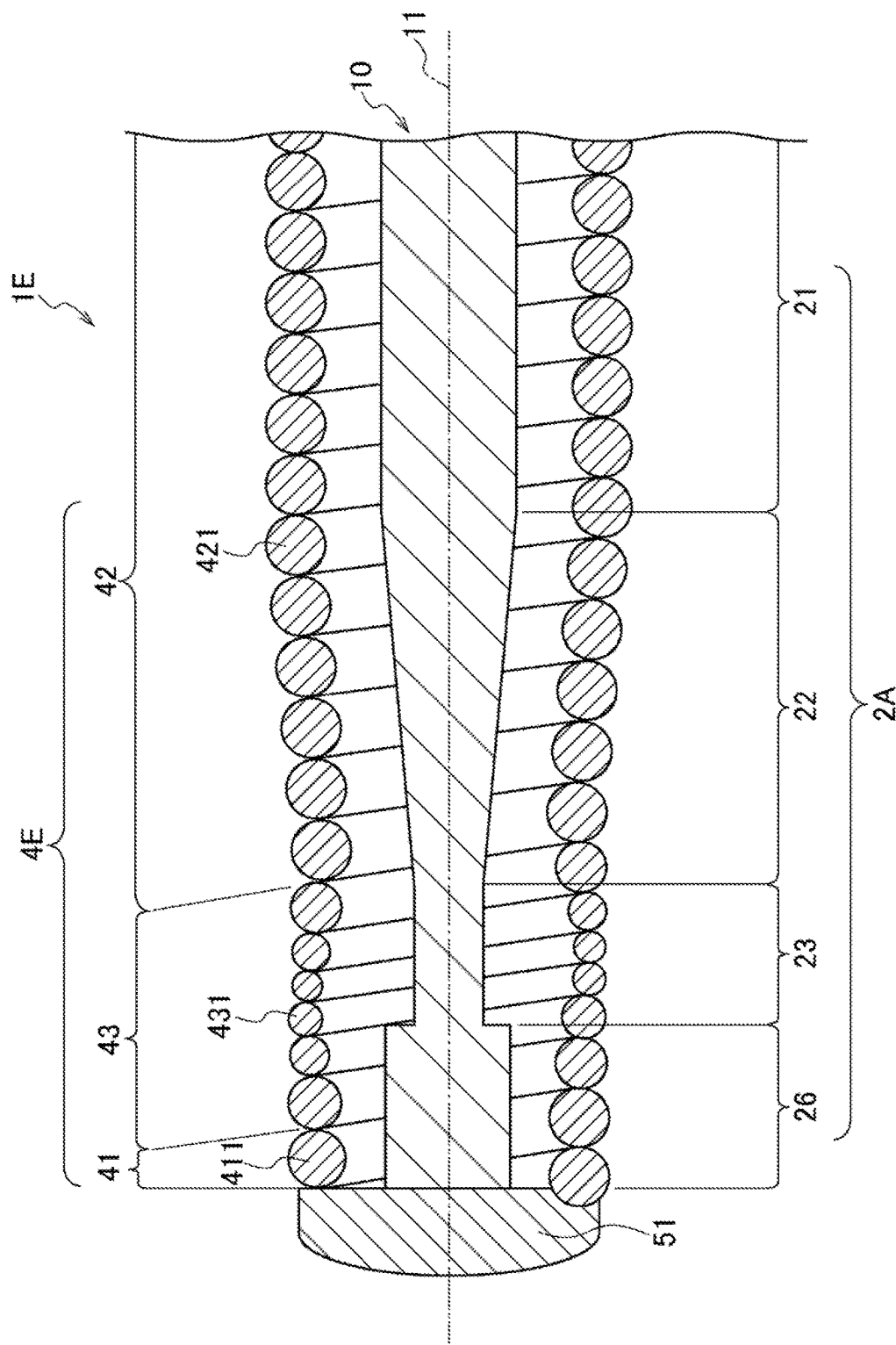
FIG. 9 is a cross-sectional view illustrating a guide wire according to a second modified example of the second exemplary embodiment.

FIG. 9 is a cross-sectional view illustrating a guide wire according to a second modified example of the second exemplary embodiment.

Similar to FIG. 7, FIG. 9 corresponds to an enlarged view illustrating a distal portion of the guide wire according to this second modified example in an enlarged manner.

In a guide wire 1E according to the second modified example, a first wire 2A includes a first constant-diameter portion 21, second constant-diameter portion 23, a first tapered portion 22, and a flat plate portion 26. That is, in comparison to the first wire 2 described above with reference to FIG. 1 and FIG. 2, the first wire 2A of this modified example further includes the flat plate portion 26. The flat plate portion 26 is located on a distal side of the second constant-diameter portion 23, and is formed in a flat plate or planar shape. The first constant-diameter portion 21, the first tapered portion 22, the second constant-diameter portion 23, and the flat plate portion 26 are disposed in this order from a proximal side of the first wire 2A to a distal side thereof. That is, the flat plate portion 26 is disposed on a further distal side in comparison to the second constant-diameter portion 23, and is connected to the second constant-diameter portion 23.

The flat plate portion 26 has a flat plate shape (ribbon shape), and may be used in a state of being deformed (reshaping: shape application) into a desired shape. That is, in some uses, an operator may bend a distal portion of the guide wire into a desired shape in advance so as to allow a distal portion of a catheter and the like, which are guided, to correspond to a shape of a blood vessel, or so as to smoothly guide the distal portion to a bifurcated blood vessel. In this manner, bending of the distal portion of the guide wire into a desired shape is called reshaping or preliminary shaping.

Although not particularly limited, the length of the flat plate portion 26 is preferably approximately 5 to 200 mm, and more preferably approximately 10 to 150 mm.

A coil intermediate portion 43 of the coil 4E is provided at a position that overlaps a portion (a boundary portion between the second constant-diameter portion 23 and the flat plate portion 26) in which the second constant-diameter portion 23 is connected to the flat plate portion 26 in a direction along the longitudinal axis 11 of the wire main body 10. That is, the coil intermediate portion 43 of this modified example is disposed to cover the vicinity of the boundary portion between the second constant-diameter portion 23 and the flat plate portion 26. The other structures are the same as the structures of the guide wire 1C described above with reference to FIG. 6 and FIG. 7.

According to this second modified example, the coil intermediate portion 43 is provided at a position that overlaps a portion in which the second constant-diameter portion 23 and the flat plate portion 26 are connected to each other and to which a stress is concentrated when the guide wire 1E is thrust in. Accordingly, when the guide wire 1E reaches the CTO lesion 62 and is thrust in, the coil intermediate portion 43 is likely to become the origin of curving in the guide wire 1E. That is, the guide wire 1E is likely to be curved at the coil intermediate portion 43 that is provided at a position that overlaps a portion in which the second constant-diameter portion 23 and the flat plate portion 26 connected to each other. According to this, when the guide wire 1E reaches the CTO lesion 62 and is thrust in, it is possible to curve the guide wire 1E at a desired position, and thus occurrence of blood vessel perforation is suppressed. In addition, it is possible to perform reshaping in an easy and reliable manner, and thus operability when the guide wire 1E is inserted into a catheter or a living body is significantly improved.

Hereinbefore, the exemplary embodiments and modifications of the disclosure have been described. However, the invention is not limited to the exemplary embodiments, and various modifications can be made in a range not departing from the scope of the appended claims. A part of the configurations of the above-described exemplary embodiments may be omitted, or the configurations may be arbitrarily combined to be different from the above description.

The detailed description above describes embodiments and modifications of a guide wire and a method representing examples of the inventive guide wire and method disclosed here. The invention is not limited, however, to the precise embodiments and modifications described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A guide wire comprising:
a flexible long wire main body; and
a coil comprised of a plurality of wires wound in a spiral shape, and disposed about an outer periphery of a distal portion of the wire main body to cover the distal portion of the wire main body,
wherein the coil includes:
a coil distal portion disposed on a distal side, the coil distal portion being comprised of one of the plurality of wires that possesses a first wire diameter and that is wound in the spiral shape so that the coil distal portion includes a plurality of adjacent windings of the wire that possesses the first wire diameter, the one of the plurality of wires possessing the first wire diameter extending to a proximal-most end of the coil distal portion,
a coil proximal portion disposed on a proximal side in comparison to the coil distal portion, the coil proximal portion being comprised of one of the plurality of wires that possesses a second wire diameter and that is wound in the spiral shape so that the coil proximal portion includes a plurality of adjacent windings of the wire that possesses the second wire diameter, the one of the plurality of wires possessing the second wire diameter extending to a distal-most end of the coil proximal portion, the second wire diameter being uniform throughout the coil proximate portion, and
a coil intermediate portion disposed between the coil distal portion and the coil proximal portion, the coil intermediate portion being comprised of one of the plurality of wires that possesses a third wire diameter and that is wound in the spiral shape so that the coil intermediate portion includes a plurality of adjacent windings of the wire that possesses the third wire diameter, the wire that possesses the third wire diameter extending throughout the coil intermediate portion from a proximal-most end of the coil intermediate portion to a distal-most end of the coil intermediate portion, the third wire diameter throughout the coil intermediate portion being smaller than the first wire diameter and smaller than the third wire diameter.

2. The guide wire according to claim 1,
wherein the wire main body includes a small-diameter portion possessing an outer diameter that is smaller than an outer diameter of at least some other portions of the wire main body, and
the coil intermediate portion is provided at a position that overlaps at least a portion of the small-diameter portion in a direction along a longitudinal direction of the wire main body.

3. The guide wire according to claim 2,
wherein the wire main body includes a tapered portion possessing an outer diameter which is gradually reduced toward a distal direction, and which is disposed on a proximal side in comparison to the small-diameter portion and is connected to the small-diameter portion, and
the coil intermediate portion is provided at a position that overlaps a portion of the wire main body including where the tapered portion is connected to the small-diameter portion in a direction along the axis.

4. The guide wire according to claim 2,
wherein the wire main body includes a flat plate portion formed in a flat plate shape and disposed on a distal side in comparison to the small-diameter portion, the flat plate portion being connected to the small-diameter portion, and
the coil intermediate portion is provided at a position that axially overlaps a portion of the wire main body at which the small-diameter portion is connected to the flat plate portion so that a part of the coil intermediate portion surrounds the portion of the wire main body at which the small-diameter portion is connected to the flat plate portion.

5. The guide wire according to claim 1,
wherein the wire main body includes,
a small-diameter portion possessing an outer diameter that is smaller than an outer diameter of at least some other portions of the wire main body, and
a tapered portion possessing an outer diameter which is gradually reduced toward a distal direction, and which is disposed on a proximal side in comparison to the small-diameter portion, and
the coil intermediate portion is provided at a position that overlaps a proximal portion of the tapered portion in a direction along a longitudinal direction of the wire main body.

6. The guide wire according to claim 1,
wherein an outer diameter of the coil distal portion is smaller than an outer diameter of the coil proximal portion.

7. The guide wire according to claim 1,
wherein an outer diameter of the coil intermediate portion is the same as an outer diameter of the coil proximal portion and an outer diameter of the coil distal portion.

8. The guide wire according to claim 1,
wherein an inner diameter of the coil intermediate portion is the same as an inner diameter of the coil proximal portion and an inner diameter of the coil distal portion.

9. The guide wire according to claim 8, wherein a clearance between an inner surface of the coil and the wire main body is constant.

10. The guide wire according to claim 1,
wherein an imaginary line connecting a center, in transverse cross-section, of each of the plurality of wires of the coil, is parallel to a longitudinal axis of the wire main body.

11. The guide wire according to claim 1, wherein the first wire diameter and the second wire diameter are equal.

12. A guide wire comprising:
a flexible long wire main body; and
a coil comprised of at least one wire wound in a spiral shape, and disposed about an outer periphery of a distal portion of the wire main body to cover the distal portion of the wire main body,
the coil including:
a coil distal portion disposed on a distal side, the coil distal portion possessing oppositely disposed proximal and distal ends, the coil distal portion including a plurality of adjacent windings of the at least one wire at a proximal-most end portion of the coil distal portion,
a coil proximal portion disposed on a proximal side in comparison to the coil distal portion, the coil proximal portion possessing oppositely disposed proximal and distal ends, the coil proximal portion including a plurality of adjacent windings of the at least one wire at a distal-most end portion of the coil proximal portion, and
a coil intermediate portion disposed between the coil distal portion and the coil proximal portion, the coil intermediate portion including a plurality of adjacent windings of the at least one wire that extend from a proximal-most end of the coil intermediate portion to a distal-most end of the coil intermediate portion, the at least one wire, throughout the coil intermediate portion, having a lamest wire diameter smaller than a wire diameter of the at least one wire forming the adjacent windings at the distal-most end portion of the coil proximal portion and smaller than a wire diameter of the at least one wire forming the adjacent windings at the proximal-most end portion of the coil distal portion.

* * * * *